United States Patent
Yu

(10) Patent No.: US 10,759,743 B2
(45) Date of Patent: Sep. 1, 2020

(54) PD-CATALYZED γ-C(SP³)-H ARYLATION / HETEROARYLATION OF FREE AMINES

(71) Applicant: The Scripps Research Institute, La Jolla, CA (US)

(72) Inventor: Jin-Quan Yu, San Diego, CA (US)

(73) Assignee: THE SCRIPPS RESEARCH INSTITUTE, La Jolla, CA (US)

(*) Notice: Subject to any disclaimer, the term of this patent is extended or adjusted under 35 U.S.C. 154(b) by 0 days.

(21) Appl. No.: 16/344,092

(22) PCT Filed: Oct. 19, 2017

(86) PCT No.: PCT/US2017/057434
§ 371 (c)(1),
(2) Date: Apr. 23, 2019

(87) PCT Pub. No.: WO2018/080897
PCT Pub. Date: May 3, 2018

(65) Prior Publication Data
US 2019/0241508 A1 Aug. 8, 2019

Related U.S. Application Data

(60) Provisional application No. 62/411,978, filed on Oct. 24, 2016.

(51) Int. Cl.

| | |
|---|---|
| *C07C 211/35* | (2006.01) |
| *C07C 211/03* | (2006.01) |
| *C07C 269/04* | (2006.01) |
| *C07D 215/12* | (2006.01) |
| *C07C 209/68* | (2006.01) |
| *C07D 213/40* | (2006.01) |
| *C07D 213/61* | (2006.01) |
| *C07B 37/04* | (2006.01) |
| *B01J 31/22* | (2006.01) |
| *C07D 213/64* | (2006.01) |
| *C07D 241/42* | (2006.01) |
| *C07D 319/18* | (2006.01) |
| *C07D 333/22* | (2006.01) |
| *C07D 471/04* | (2006.01) |

(52) U.S. Cl.
CPC ......... *C07C 269/04* (2013.01); *B01J 31/2239* (2013.01); *C07B 37/04* (2013.01); *C07C 209/68* (2013.01); *C07D 213/40* (2013.01); *C07D 213/61* (2013.01); *C07D 213/64* (2013.01); *C07D 215/12* (2013.01); *C07D 241/42* (2013.01); *C07D 319/18* (2013.01); *C07D 333/22* (2013.01); *C07D 471/04* (2013.01); *B01J 2231/44* (2013.01); *B01J 2531/824* (2013.01); *C07C 2601/08* (2017.05); *C07C 2601/14* (2017.05); *C07C 2601/18* (2017.05)

(58) Field of Classification Search
CPC .......................... C07C 211/03; C07C 211/35
USPC .................................................. 564/462, 463
See application file for complete search history.

(56) References Cited

FOREIGN PATENT DOCUMENTS

| WO | WO-2015131100 A1 | 9/2015 |
|---|---|---|
| WO | WO-2016123361 A1 | 8/2016 |
| WO | WO-2018080897 A1 | 5/2018 |

OTHER PUBLICATIONS

"International Application Serial No. PCT/US2017/057434, International Preliminary Report on Patentability dated May 9, 2019", 5 pgs.
"International Application Serial No. PCT/US2017/057434, International Search Report dated Jan. 5, 2018", 2 pgs.
"International Application Serial No. PCT/US2017/057434, Written Opinion dated Jan. 5, 2018", 3 pgs.
Liu, Yongbing, et al., "Site-Selective C—H Arylation of Primary Aliphatic Amines Enabled by a Catalytic Transient Directing Group", Nature Chemisty, vol. 9, (Jan. 2007), 26-32.
Zhang, Fang-Lin, et al., "Functionalization of C(sp3)-H Bonds Using a Transient Directing Group", Science, vol. 351, Issue 6270, (Jan. 15, 2016), 252-256.

*Primary Examiner* — Douglas M Willis
(74) *Attorney, Agent, or Firm* — Schwegman Lundberg & Woessner, P.A.

(57) ABSTRACT

Pd(II)-catalyzed g-G(sp3)-H arylation or heteroarylation of primary amines is realized by using 2-hydroxynicotinaldehyde as a catalytic transient directing group. Importantly, the catalyst and the directing group loading can be lowered to 2% and 4% respectively, thus demonstrating high efficiency of this newly designed transient directing group. Heterocyclic aryl iodides are also compatible with this reaction. Furthermore, swift synthesis of 1,2,3,4-tetrahydronaphthyridine derivatives is accomplished using this reaction.

11 Claims, No Drawings

PD-CATALYZED γ-C(SP³)-H ARYLATION / HETEROARYLATION OF FREE AMINES

CROSS-REFERENCE TO RELATED APPLICATION

This application claims the priority of U.S. provisional application Ser. No. 62/411,978, filed Oct. 24, 2016, the disclosure of which is incorporated by reference herein in its entirety.

STATEMENT OF GOVERNMENT SUPPORT

This invention was made with government support under 2R01GM084019 awarded by the National Institutes of Health. The government has certain rights in the invention.

BACKGROUND

In the past decade, directed C—H activations have been extended to a wide range of synthetically useful substrates and transformations.[1] Nevertheless, the covalent installation and removal of directing groups often poses a major obstacle for their synthetic applications. In addition to adding two steps to the synthetic sequence, the reaction conditions for these steps are sometimes incompatible with labile functionalities on advanced synthetic intermediates.

Thus, developing catalytic directing groups that can transiently bond to the substrate for C—H activation and subsequently dissociate reversibly is highly desirable. This strategy has been successfully applied in a number of Rh(I)-catalyzed C(sp²)-H activations.[2] Recently, our group discovered that simple amino acids can serve as an effective transient directing group for Pd(II)-catalyzed C(sp³)-H functionalization of aldehydes and ketones via a reversible imine linkage, thus demonstrating the feasibility of using transient directing groups for Pd(II) catalysts, although the loading of directing groups is still high (40%).[3] Notably, the bicentate coordination system provided by the imine moiety and the weakly coordinating carboxylic acid points to a new direction for our long search of transient directing groups that assist the activation of C(sp³)-H bonds (Scheme 1(2)).

Following the success of identifying a transient directing group for ketones, we wondered whether similar approach could be applied for the activation of free amines. Amines are ubiquitous structural motifs in compounds with pharmaceutical, agrochemical and agricultural importance.[4] While site-selective C—H functionalization of free aliphatic amine is highly desirable as it enables rapid late-stage modifications and derivations, this process is traditionally difficult due to the formation of the unreactive $Pd(RNH_2)_2X_2$ complexes,[5] as well as the vulnerability of amines towards a-oxidation and electrophiles.[6] Nevertheless, numerous methods have been developed for the C—H functionalization of amines with various protecting groups.[7-9] An interesting b-C—H functionalization of free secondary amines ($R_2NH$) has also been reported, although bulky a-quaternary center is required for this reaction.[10]

SUMMARY

In various embodiments, the it provides a method for Pd(II)-catalyzed g-C(sp³)-H arylation or heteroarylation of a primary amine having a γ-hydrogen atom, using an effective amount of a catalytic transient directing group of formula TDG

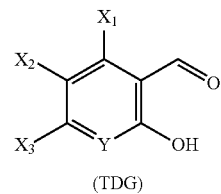

(TDG)

wherein Y is N or $CX_4$; and $X_1$, $X_2$, $X_3$, and $X_4$ each independently is alkyl, aryl, haloalkyl, alkylamino, or alkoxyl; or wherein any single pair of $X_1$ and $X_2$, of $X_2$ and $X_3$, and of $X_3$ and $X_4$ when present, together with the ring to which they are bonded, forms a fused 5-, 6-, or 7-membered cycloalkyl ring;

the method comprising contacting a primary amino compound of formula (I)

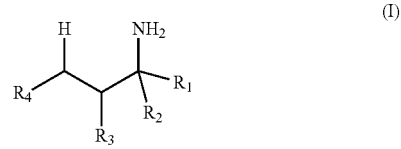

wherein $R_1$, $R_2$, $R_3$, and $R_4$ each independently is hydrogen or alkyl, or wherein $R_2$ and $R_4$ together with the atoms to which they are bonded form a cycloalkyl, and an aryl iodide (ArI) or a heteroaryl iodide (HetArI), respectively, which can be unsubstituted or can be substituted with one or more independently selected aryl, alkyl, halo, nitro, haloalkyl, alkoxyl, alkoxycarbonyl, or carboxaldehyde groups;

in the presence of an effective amount of palladium(II) acetate, $Pd(II)(OAc)_2$, and in the presence of an effective amount of transient directing group TDG, to provide a product of formula (II)

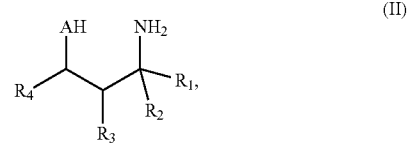

wherein AH signifies an aryl or a heteroaryl group.

Further, the invention provides, in various embodiments, a method wherein the compound of formula (II) is further N-protected with a t-butoxycarbonyl (tBoc) group by contacting the compound of formula (II) and t-butoxycarbonylanhydride, to give a compound of formula (III)

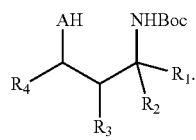
(III)

For instance, the TDG can be 2-hydroxynicotinaldehyde (TDG4).

In various embodiments, the primary amino compound of formula (I) can be contacted with an aryl iodide and group AH in the compound of formula (II) can be aryl. More specifically, the reaction milieu can further comprise silver trifluoroacetate. More specifically, the group AH in the compound of formula (III) can be aryl.

In various embodiments, the primary amino compound of formula (I) can be contacted with a heteroaryl iodide and group AH in the compound of formula (II) can be heteroaryl. More specifically, the reaction milieu can further comprise silver trifluoroacetate or pyridone, or both. More specifically, the group AH in the compound of formula (III) can be heteroaryl.

In various embodiments, the compound of formula (II) or of formula (III) can be any of the examples provided, wherein group AH is aryl or is heteroaryl.

DETAILED DESCRIPTION

Herein, we report an efficient Pd-catalyzed C—H arylation or heteroarylation reaction of free primary amines with aryl iodide as coupling partners under air using a catalytic transient directing group. This development, in combination with our previous transient directing group for ketone substrates,[3] identifies imine and weakly coordinating carboxylate or its surrogate as privileged structural motifs for efficient transient directing groups. Scheme 1 compares this known ketone γ-sp3 arylation procedure (1) with the method disclosed and claimed herein (2).

Using 2-hydroxynicotinaldehyde as a catalytic transient directing group, arylation of the γ-carbon atom of an alkylamino substrate having a γ-hydrogen atom can be achieved in good yield.

Scheme 1

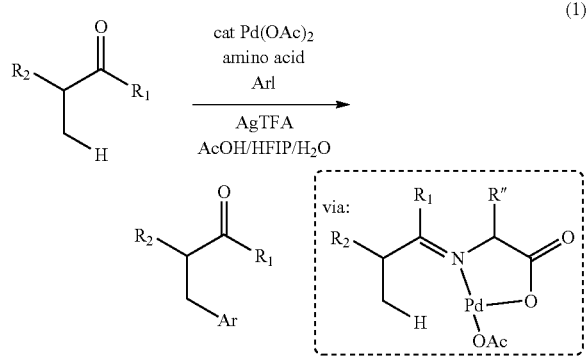
(1)

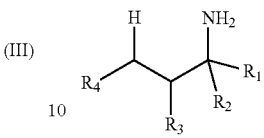 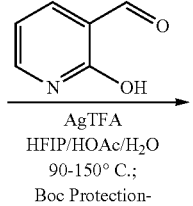
(2)

this work:

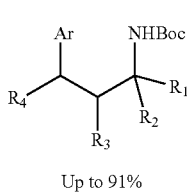

Up to 91%

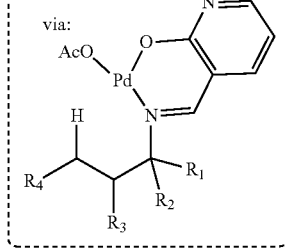

Inspired by Jun's Rh(I)-catalyzed aldehydic C—H activation using a reversible imine/pyridine directing group,[2a] we have previously investigated the development of imine/chiral oxazoline[11] transient directing groups for asymmetric C—H activation of ketones and amines without success. Recently, Dong's group reported an interesting example of g-arylation of free primary amines via in situ generation of an imine directing group with stoichiometric 8-formylquinoline.[12]

However, this method is mostly limited to amines containing a-substituents and requires using highly active aryl iodonium $Ar_2IBF_4$ salts as coupling partners. The use of glovebox is also necessary, presumably to prolong the lifetime of the stoichiometric imines. From our previous studies on imine/oxazoline and imine/pyridine transient directing groups, we believe that these strongly coordinating transient directing groups have two fundamental disadvantages for rendering the directing group catalytic: undesired strong bischelation of amino/oxazoline or pyridine with Pd(II) prevents the required formation of the imine linkage; the imine/oxezoline or pyridine bischelation with Pd(II), even if generated, is not sufficiently reactive for developing highly effective catalytic directing groups.

Since the combination of the imine moiety and the weakly coordinating carboxyl group constitutes an efficient transient directing group for ketones (Eq 1), we envisioned a-keto acids could form similar transient intermediates upon condensation with amine substrates (Table 1). Cyclohexylamine was chosen as model substrate due to its abundancy and relative high boiling point. Boc protection of the arylated amine was performed for ease of separation and analysis. Our initial experimental exploration was largely based on our previous reaction conditions.[3] 10 eq of $H_2O$ was added to facilitate the imine hydrolysis after C—H activation. We were encouraged to find that trace amount of arylated product $2a_{19}$ was detected with glyoxylic acid (TDG1).[13] Slightly improved yield was obtained when glyoxylic acid was replaced with the more stable phenylglyoxylic acid (TDG2). Gratifyingly, replacing the carboxyl group with an acidic phenol afforded the desired product in 62% yield (TDG3). Since 2-hydroxypyridine (pyridone) has been used as carboxyl surrogate in our previous ligand design for meta-C—H activation,[14] we tested commercially available 2-hydroxynicotinaldehyde as the catalytic transient directing group. To our delight, the reaction proceeded to completion and afforded 2a[19] in 94% yield (TDG4). Introducing an electron-withdrawing $CF_3$ group to the hydroxypyridine directing group reduced the yield (TDG5). TDG6 was completely unreactive, which suggests that the 7-membered ring bischelation is not reactive. Other bidentate coordination systems such as the imine/pyridine and imine/quinoline systems provided negligible yields regardless the involvement of the 5-membered or the 6-membered ring bischelation (TDG7-8), confirming the importance of the weakly coordinating anionic hydroxyl group.

TABLE 1

Development of the Transient Directing Group[a, b]

Transient Directing Groups (TDG)

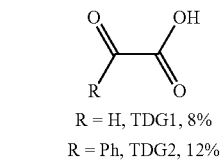

R = H, TDG1, 8%
R = Ph, TDG2, 12%

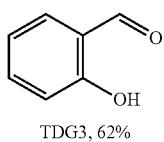

TDG3, 62%

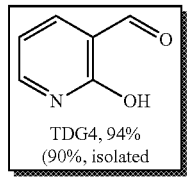

TDG4, 94%
(90%, isolated)

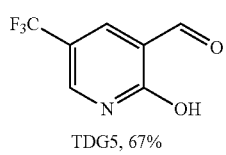

TDG5, 67%

TABLE 1-continued

Development of the Transient Directing Group[a, b]

TDG6, <5%

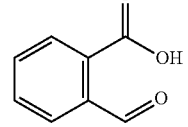

TDG7, <5%

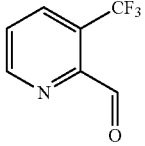

TDG8, 8%

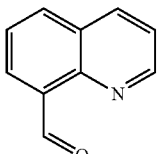

NR

TDG9, <5

[a]Conditions: 1a (0.2 mmol), 4-CO₂MePhI (0.4 mmol), Pd(OAc)₂ (10 mol %), TDG (20 mol %), AgTFA (0.4 mmol), HFIP/HOAc = 19/1 (1.0 mL), H₂O (2.0 mmol), 120° C., 12 h.
[b]Yields were determined by ¹H NMR analysis of the crude reaction mixture using CH₂Br₂ as the internal standard.

A series of control experiments were also conducted. The reaction did not proceed in the absence of the transient directing group. Simple 2-hydroxypyridine did not give any product, which confirms the importance of the imine generation. Furthermore, the bidentate chelation mode of the imine and hydroxyl moieties in TDG4 was also shown to be crucial in this reaction as changing their spatial arrangements provided trace products (TDG 9).

With the optimized conditions in hand, we next investigated the scope of the aryl iodide coupling partners. We were pleased to find that γ-C(sp$^3$)-H arylation of 1a with a vast variety of aryl iodides proceeded smoothly to provide an efficient access of 3-aryl cyclohexylamines with good to excellent yields (Table 2), which were found to be applicable in the synthesis of potent antitumor reagents.[15] Simple iodobenzene and various other methyl and phenyl substituted aryl iodides are well tolerated, affording the desired products in excellent yields (2a$_1$-2a$_5$). Electron rich aryl iodides with alkoxy substituents afforded the corresponding products in good yields (2a$_6$-2a$_8$). Halogenated aryl iodides containing fluoro, chloro and bromo substituents are also tolerated (2a$_9$-2a$_{11}$, 2a$_{13}$-2a$_{14}$). When 1,3-diiodobenzene was employed as the coupling partner, only one iodide was activated (2a$_{12}$). Electron deficient aryl iodides bearing trifluoromethyl, nitro, methyl ketone and ester substituents are all well tolerated, providing consistently good to excellent yields (2a$_{15}$-2a$_{17}$, 2a$_{19}$). Notably, reactive aldehyde functionality on the aryl iodide remained intact during the reaction (2a$_{18}$). Furthermore, sterically demanding aryl iodides bearing substitutions at the ortho position are also compatible with this protocol (2a$_7$, 2a$_9$, 2a$_{11}$). While arylation of cyclohexylamine with heterocyclic aryl iodide gave less than 10% yield, acyclic alkyl amine displayed excellent compatibility with a range of heteroaryl iodides. Pyridine based aryl iodides with different substitutions such as fluoro, chloro, bromo and trifluoromethyl groups at different positions are well tolerated, providing 50-70% yields (2b$_1$-2b$_6$, 2b$_8$). Even electron donating methoxy group is also compatible (2b$_7$). Various other thiophene, quinoline and quinoxaline based heterocyclic aryl iodides are also tolerated, providing moderate yields (2b$_9$-2b$_{12}$).

TABLE 2

Scope of Aryl Iodide Coupling Partners$^{a, b}$

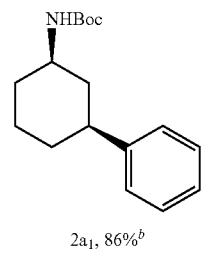 [SMILES: CC(C)(C)OC(=O)N[C@@H]1CCC[C@H](c2ccccc2)C1]

2a$_1$, 86%$^b$

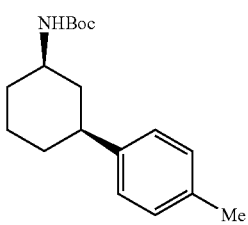

2a$_2$, 91%

TABLE 2-continued

Scope of Aryl Iodide Coupling Partners$^{a, b}$

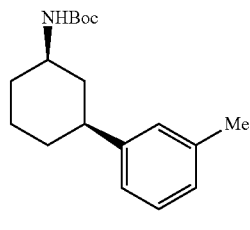

2a$_3$, 91%

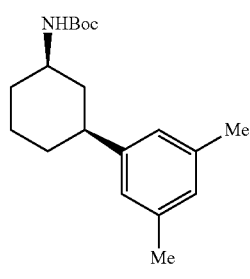

2a$_4$, 88%

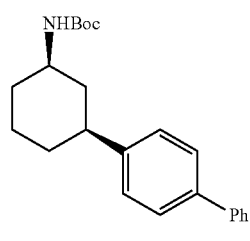

2a$_5$, 83%

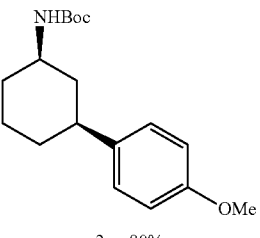

2a$_6$, 80%

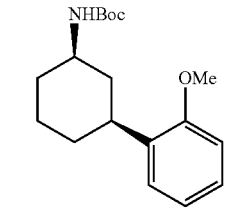

2a$_7$, 65%

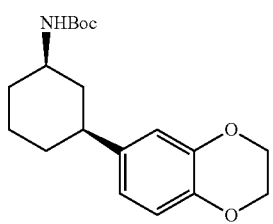

2a$_8$, 75%

TABLE 2-continued
Scope of Aryl Iodide Coupling Partners[a,b]
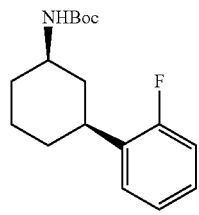
2a9, 63%
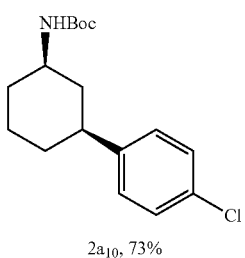 [SMILES: CC(C)(C)OC(=O)N[C@@H]1CCC[C@H](c2ccc(Cl)cc2)C1]
2a10, 73%
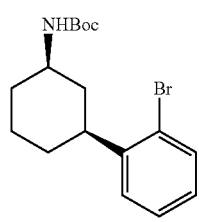
2a11, 61%
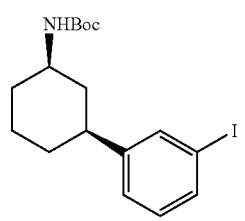
2a12, 61%
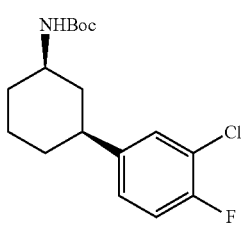
2a13, 74%
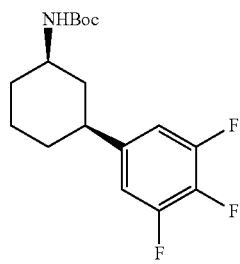
2a14, 52%
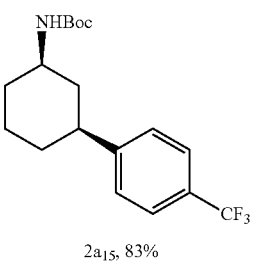 [SMILES: CC(C)(C)OC(=O)N[C@@H]1CCC[C@H](c2ccc(C(F)(F)F)cc2)C1]
2a15, 83%
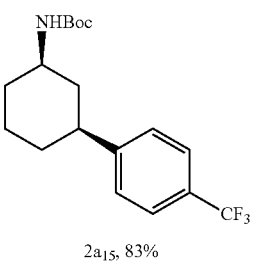 [SMILES: CC(C)(C)OC(=O)N[C@@H]1CCC[C@H](c2ccc(C(F)(F)F)cc2)C1]
2a16, 73%
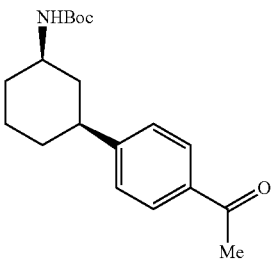
2a17, 80%
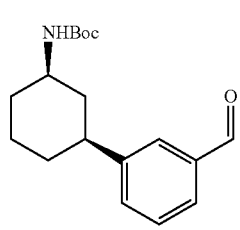
2a18, 63%

TABLE 2-continued

Scope of Aryl Iodide Coupling Partners[a, b]

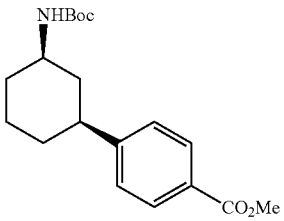

2a₁₉, 90%

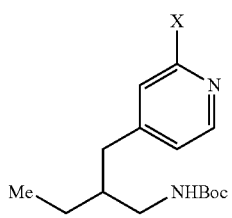

2b₁, X = F, 66%
2b₂, X = Cl, 69%
2b₃, X = Br, 56%

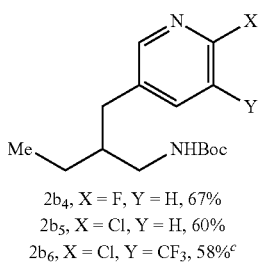

2b₄, X = F, Y = H, 67%
2b₅, X = Cl, Y = H, 60%
2b₆, X = Cl, Y = CF₃, 58%[c]

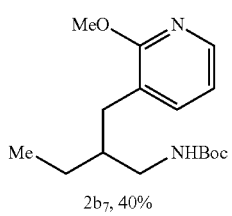

2b₇, 40%

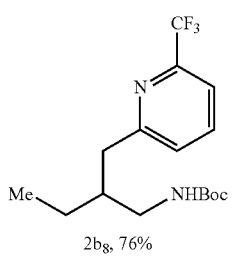

2b₈, 76%

2b₉, 43%[c]

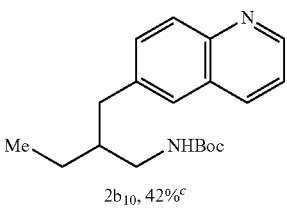 [SMILES: CCC(CNC(=O)OC(C)(C)C)Cc1ccc2ncccc2c1]

2b₁₀, 42%[c]

TABLE 2-continued

Scope of Aryl Iodide Coupling Partners[a, b]

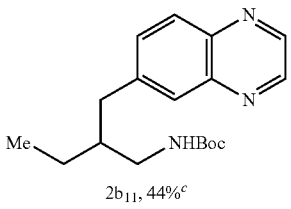

2b₁₁, 44%[c]

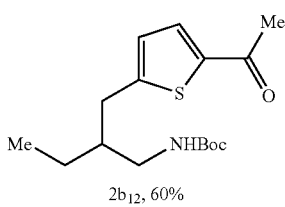 [SMILES: CCC(CNC(=O)OC(C)(C)C)Cc1ccc(C(C)=O)s1]

2b₁₂, 60%

[a]Conditions: 1a-b (0.2 mmol), ArI (0.4 mmol), Pd(OAc)₂ (10 mol %), TDG4 (20 mol %), AgTFA (0.4 mmol), HFIP/HOAc = 19/1 (1.0 mL), H₂O (2.0 mmol), 120° C., 12 h.
[b]Isolated yields.
[c]130° C., 48 h.

Next we surveyed the amine scope of this g-C(sp³)-H arylation. We were pleased to find that our protocol was applicable to a variety of free aliphatic amines. The arylation of methyl C—H bonds in simple free aliphatic amines such as propylamine, isobutylamine, and 2-methylbutylamine proceeded selectively at the g position with good yields (2c-e). Aliphatic amines bearing one or two methyl groups at the a-substitution are also well tolerated (2f-g). In comparison to aliphatic amines with a-substituent, those without a-substituent are usually more difficult substrates in C—H activations,[16] which presumably attributes to both the lack of the Thorpe-Ingold effect and the increased susceptibility to oxidation and electrophiles. However, our system is effective in both a-substituted and non-substituted substrates. Various functionalities such as phenyl, ether and even additional free amine (the di-free amine was used in 2j and subsequently di-Boc protected) are compatible with this catalytic system, providing the corresponding products in moderate yields (2h-j). Furthermore, methylene C—H arylations of both cyclic and acyclic substrates are achieved. Simple acyclic aliphatic amines of different lengths and bearing methyl a-substitution proceeded with moderate to good efficiencies (2k-l, 2m). Cyclic amines such as cyclopentyl- and cyclooctyl-amines are also tolerated, affording the desired products as a single diastereomer (2n-o).

To demonstrate the synthetic utility of this reaction, we were pleased to find that the catalyst and directing group loading can be lowered to sub 5%, thus rendering the transient directing group catalytic (Scheme 2a). When the reaction was scaled up to 2 mmol, the catalyst and template could be further lowered to 2% and 4% respectively. The desired pure arylated free amine product could be obtained in 61% isolated yield following simple acid-base extraction protocols without any further purification (Scheme 2b). Furthermore, the C—H arylation of 1b with 2-fluoro-4-iodopyridine provides a facile access to 1,2,3,4-tetrahydronaphthyridine derivatives, which exhibit important biological activities.[17] S_NAr of amine to the pyridyl fluoride spontaneously took place in a one-pot fashion without any reaction work up, affording 2q in 70% isolated yield (Scheme 2c).

Scheme 2. Scale up Reaction and Synthetic Applications

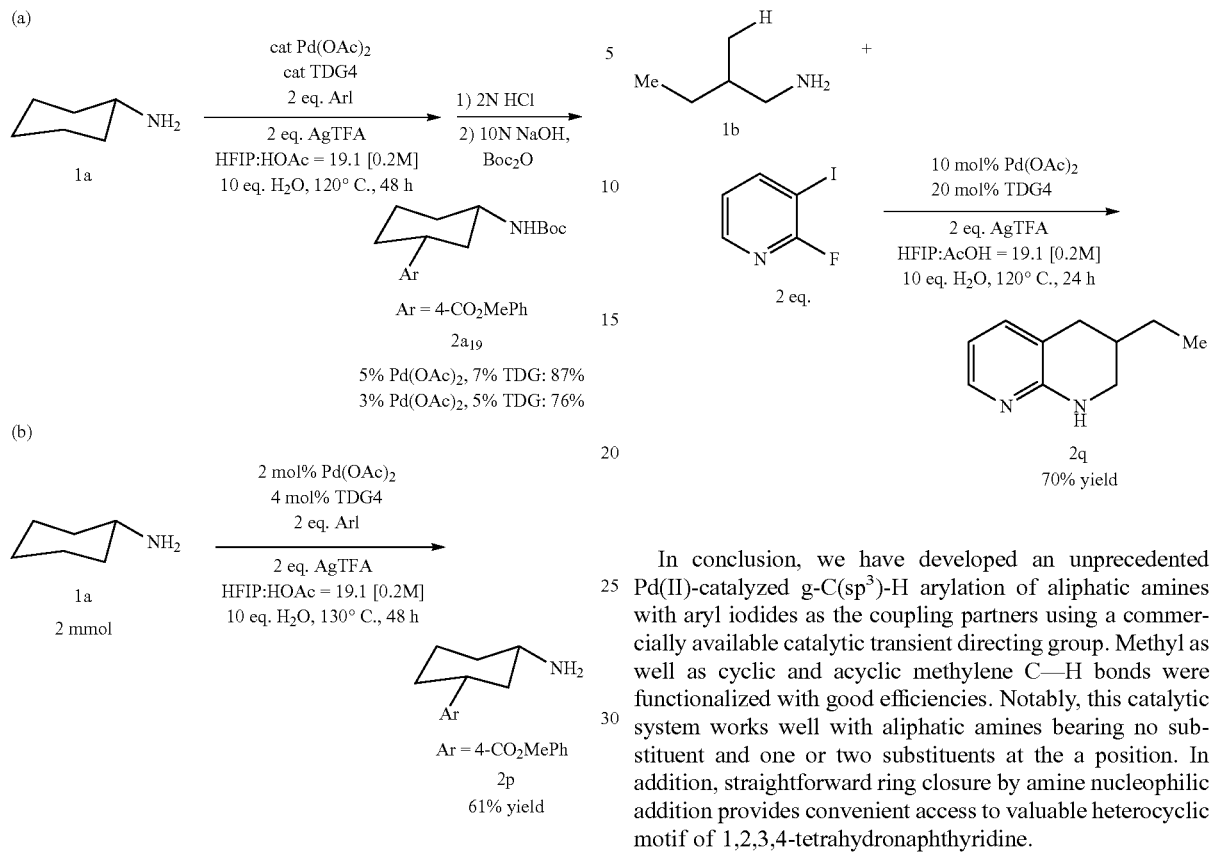

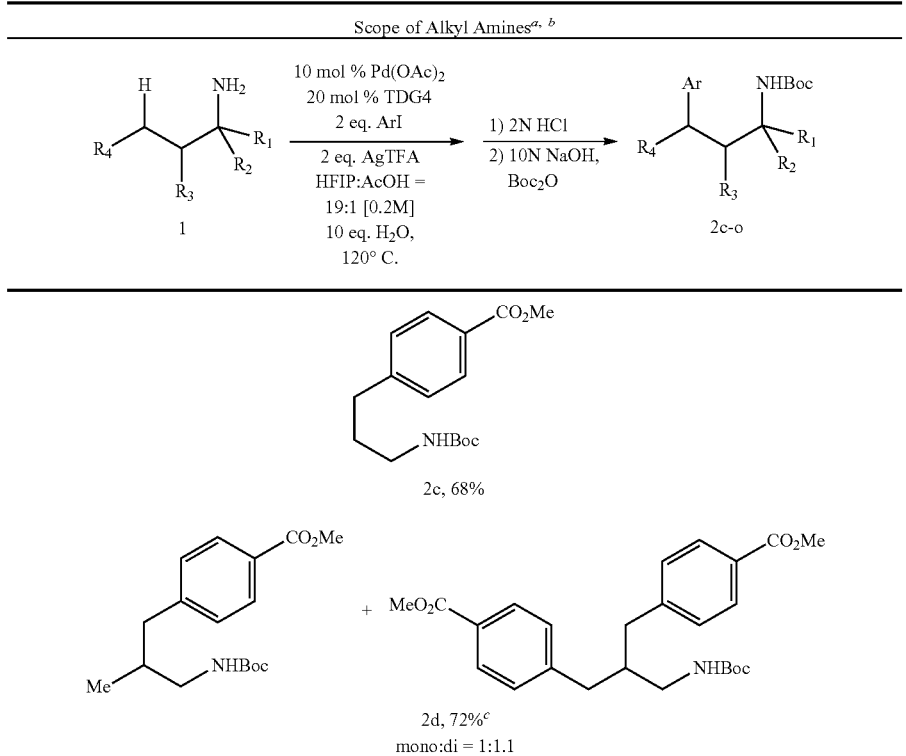

In conclusion, we have developed an unprecedented Pd(II)-catalyzed g-C(sp$^3$)-H arylation of aliphatic amines with aryl iodides as the coupling partners using a commercially available catalytic transient directing group. Methyl as well as cyclic and acyclic methylene C—H bonds were functionalized with good efficiencies. Notably, this catalytic system works well with aliphatic amines bearing no substituent and one or two substituents at the a position. In addition, straightforward ring closure by amine nucleophilic addition provides convenient access to valuable heterocyclic motif of 1,2,3,4-tetrahydronaphthyridine.

TABLE 3-continued
Scope of Alkyl Amines[a, b]
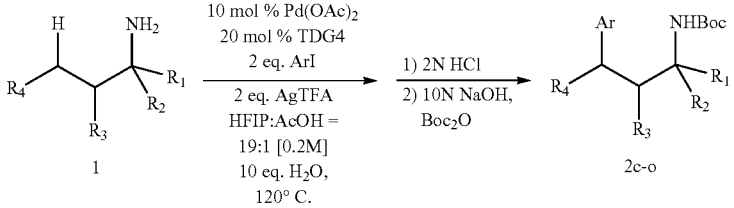
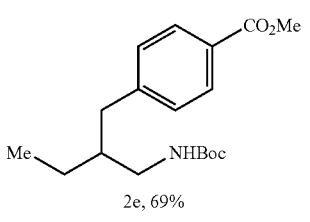
2e, 69%
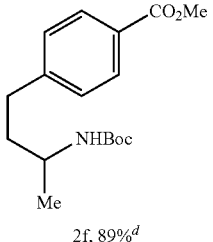
2f, 89%[d]
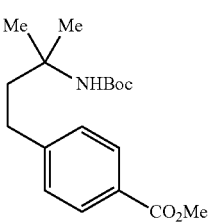
2g, 61%
mono:di (1:2.8)
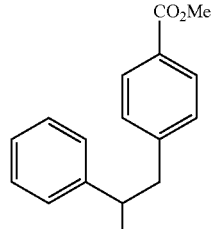
2h, 60%
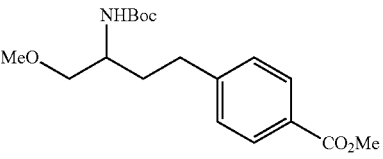
2i, 51%
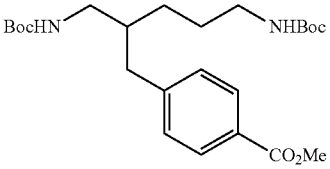
2j, 46%
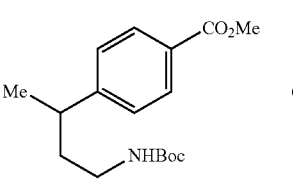
2k, 66%[e]
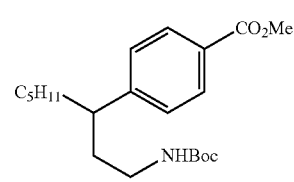
2l, 43%[e]
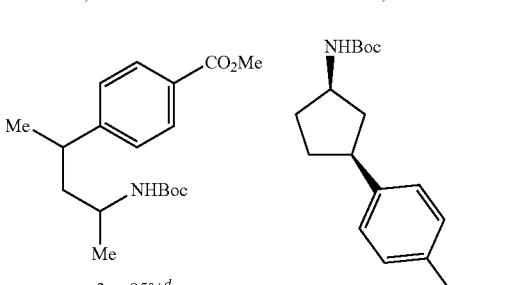
2m, 85%[d]
d.r 2.6:1
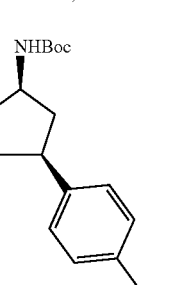
2n, 41%[d]

TABLE 3-continued

Scope of Alkyl Amines[a, b]

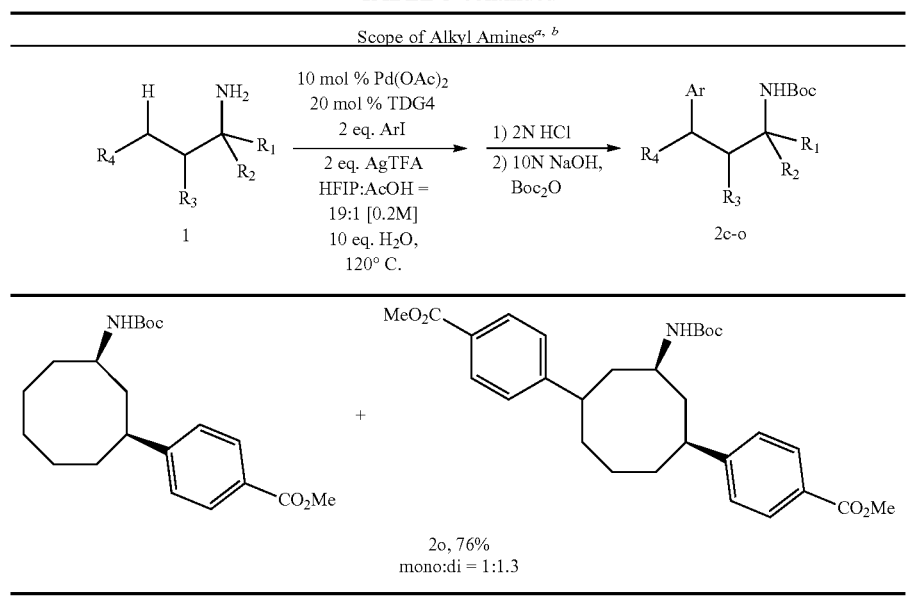

2o, 76%
mono:di = 1:1.3

[a]Conditions: 1c-o (0.2 mmol), 4-CO₂MePhI (0.4 mmol), Pd(OAc)₂ (10 mol %), TDG4 (20 mol %), AgTFA (0.4 mmol), HFIP/HOAc = 19/1 (1.0 mL), H₂O (2.0 mmol), 120° C., 12 h.
[b]Isolated yields.
[c]90° C.
[d]50 mol % TDG4.
[e]150° C., HFIP/HOAc = 2:1, 30 eq H₂O.

In the various embodiments of the heteroarylation reaction analogous to the above-described arylation reaction, the following scheme illustrates the method. The reaction can be carried out using TDG and silver trifluoroacetate, as described above, further in the presence of pyridine, in the condensation of an amino compound possessing a γ-hydrogen atom and a heteroaryl iodide as shown in Scheme 3, below.

Scheme 3: Heteroarylation reaction

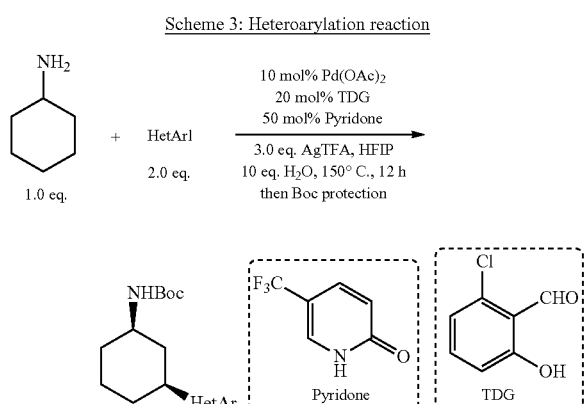

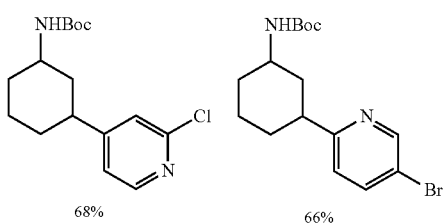

Conditions: Cyclohexyl amine (0.1 mmol), Heteroaryl Iodides (0.2 mmol), Pd(OAc)₂ (0.01 mmol), TDG (0.02 mmol), pyridone (0.05 mmol), AgOTFA (0.3 mmol), H₂O (1.0 mmol), HFIP (1.0 mL), 150° C., 12 h. After the completion of the reaction, the amine product was protected with Boc₂O Various heteroaryliodides can be used in this reaction, for example as shown in Table 4, wherein group R can be any of aryl, alkyl, halo, nitro, haloalkyl, alkoxyl, alkoxycarbonyl, or carboxaldehyde groups.

TABLE 4

Heteroaryl iodide reagents

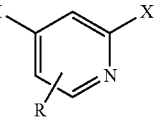

TABLE 4-continued

Heteroaryl iodide reagents

[Structures of heteroaryl iodide reagents shown]

DOCUMENTS CITED (1) For selected reviews, see: (a) Chen, X.; Engle, K. M.; Wang, D.-H.; Yu, J.-Q. *Angew. Chem., Int. Ed.* 2009, 48, 5094. (b) Daugulis, O.; Do, H.-Q.; Shabashov, D. *Acc. Chem. Res.* 2009, 42, 1074. (c) Lyons, T. W.; Sanford, M. S. *Chem. Rev.* 2010, 110, 1147. (d) Colby, D. A.; Bergman, R. G.; Ellman, J. A. *Chem. Rev.* 2010, 110, 624. (e) Arockiam, P. B.; Bruneau, C.; Dixneuf, P. H. *Chem. Rev.* 2012, 112, 5879. (f) Huang, Z.; Lim, H. N.; Mo, F.; Young, M. C.; Dong, G. *Chem. Soc. Rev.* 2015, 44, 7764.

(2) For leading references, see: (a) Jun, C.-H.; Lee, H.; Hong, J.-B. *J. Org. Chem.* 1997, 62, 1200. (b) Bedford, R. B.; Coles, S. J.; Hursthouse, M. B.; Limmert, M E. *Angew. Chem., Int. Ed.* 2003, 42, 112. (c) Grünanger, C. U.; Breit, B. *Angew. Chem. Int. Ed.* 2008, 47, 7346. (d) Lightburn, T. E.; Dombrowski, M. T.; Tan, K. L. *J. Am. Chem. Soc.* 2008, 130, 9210. (e) Mo, F.; Dong, G. *Science* 2014, 345, 68.

(3) Zhang, F.-L.; Hong, K.; Li, T.-J.; Park, H.; Yu, J.-Q. *Science* 2016, 351, 252.

(4) (a) Nugent, T. C. *Chiral Amine Synthesis: Methods, Developments and Applications,* Wiley-VCH Verlag GmbH & Co. KGaA, Weinheim, Germany, 2010. (b) Vitaku, E.; Smith, D. T.; Njardarson, J. T. *J. Med. Chem.* 2014, 57, 10257, (c) Jeanmart, S.; Edmunds, A. J. F.; Lamberth, C.; Pouliot, M. *Bioorg. Med. Chem.* 2016, 24, 317.

(5) Vicente, J.; Saura-Llamas, I.; Palin, M. G.; Jones, P. G.; Ramirez de Arellano, M. C. *Organometallics* 1997, 16, 826.

(6) (a) Corey, E. J.; Achiwa, K. *J. Am. Chem. Soc.* 1969, 91, 1429. (b) Hartwig, J. F.; Richards, S.; Barañano, D.; Paul, F. *J. Am. Chem. Soc.* 1996, 118, 3626. (c) Wolfe, J. P.; Wagaw, S.; Buchwald, S. L. *J. Am. Chem. Soc.* 1996, 118, 7215. (d) Sigman, M. S.; Eaton, B. E. *Tetrahedron Lett.* 1993, 34, 5367. Ryland, B. L.; (e) Stahl, S. S. *Angew. Chem., Int. Ed.* 2014, 53, 8824. For a review on oxidation of amine to imine, see: (f) Largeron, M. *Eur. J. Org. Chem.* 2013, 5225.

(7) For examples with amide protecting group, see: (a) Zaitsev, V. G.; Shabashov, D.; Daugulis, O. *J. Am. Chem. Soc.* 2005, 127, 13154. (b) Neumann, J. J.; Rakshit, S.; Dröge, T.; Glorius, F. *Angew. Chem., Int. Ed.* 2009, 48, 6892. (c) Shabashov, D.; Daugulis, O. *J. Am. Chem. Soc.* 2010, 132, 3965. (d) He, G.; Chen, G. *Angew. Chem., Int. Ed.* 2011, 50, 5192. (e) He, G.; Zhao, Y.; Zhang, S.; Lu, C.; Chen, G. *J. Am. Chem. Soc.* 2012, 134, 3. (f) Nadres, E. T.; Daugulis, O. *J. Am. Chem. Soc.* 2012, 134, 7. (g) Zhang, S.-Y.; He, G.; Zhao, Y.; Wright, K.; Nack, W. A.; Chen, G. *J. Am. Chem. Soc.* 2012, 134, 7313. (h) Zhang, S.-Y.; He, G.; Nack, W. A.; Zhao, Y.; Li, Q.; Chen, G. *J. Am. Chem. Soc.* 2013, 135, 2124. (i) Ye, X.; He, Z.; Ahmed, T.; Weise, K.; Akhmedov, N. G.; Petersen, J. L.; Shi, X. *Chem. Sci.* 2013, 4, 3712. (j) Fan, M.; Ma, D. *Angew. Chem., Int. Ed.* 2013, 52, 12152. (k) Zhang, L.-S.; Chen, G.; Wang, X.; Guo, Q.-Y.; Zhang, X.-S.; Pan, F.; Chen, K.; Shi, Z.-J. *Angew. Chem., Int. Ed.* 2014, 53, 3899. (l) Ling, P.-X.; Fang, S.-L.; Yin, X.-S.; Chen, K.; Sun, B.-Z.; Shi, B.-F. *Chem.-Eur. J.* 2015, 21, 17503. (m) Xu, J.-W.; Zhang, Z.-Z.; Rao, W.-H.; Shi, B.-F. *J. Am. Chem. Soc.* 2016, 138, 10750.

(8) For examples with sulfonamide protecting group, see: (a) Rodriguez, N.; Romero-Revilla, J. A.; Fernandez-Ibanez, M. A.; Carretero, J. C. *Chem. Sci.* 2013, 4, 175. (b) Chu, L.; Wang, X.-C.; Moore, C. E.; Rheingold, A. L.; Yu, J.-Q. *J. Am. Chem. Soc.* 2013, 135, 16344. (c) Chan, K. S. L.; Wasa, M.; Chu, L.; Laforteza, B. N.; Miura, M.; Yu, J.-Q. *Nat Chem* 2014, 6, 146. (d) Chu, L.; Xiao, K.-J.; Yu, J.-Q. *Science* 2014, 346, 451. (e) Chan, K. S. L.; Fu, H.-Y.; Yu, J.-Q. *J. Am. Chem. Soc.* 2015, 137, 2042. (f) Jiang, H.; He, J.; Liu, T.; Yu. J.-Q. *J. Am. Chem. Soc.* 2016, 138, 2055.

(9) For examples with other protecting groups, see: (a) Espino, C. G.; Fiori, K. W.; Kim, M.; Du Bois, J. *J. Am. Chem. Soc.* 2004, 126, 15378. (b) Kim, M.; Mulcahy, J. V.; Espino, C. G.; Du Bois, J. *Org. Lett.* 2000, 8, 1073. (c) Spangler, J. E.; Kobayashi, Y.; Verma, P.; Wang, D.-H.; Yu, J.-Q. *J. Am. Chem. Soc.* 2015, 137, 11876. (d) Huang, Z.; Wang, C.; Dong, G. *Angew. Chem., Int. Ed.* 2016, 55, 5299. (e) Topczewski, J. J.; Cabrera, P. J.; Saper, N. I.; Sanford, M. S. *Nature* 2016, 531, 220.

(10) (a) McNally, A.; Haffemayer, B.; Collins, B. S. L.; Gaunt, M. J. *Nature* 2014, 510, 129. (b) He, C.; Gaunt, M. J. *Angew. Chem., Int. Ed.* 2015, 54, 15840.

(11) R. Giri, X. Chen, J.-Q. Yu, *Angew. Chem.* 2005, 117, 2150-2153; Angew. Chem. Int. Ed. 2005, 44, 2112-2115.

(12) Xu, Y.; Young, M. C.; Wang, C.; Magness, D. M.; Dong, G. *Angew. Chem., Int. Ed.* 2016, 55, 9084.

(13) While we are submitting this manuscript, g-arylation of alkyl amines using transient directing group TDG1 was reported. Y. Liu, H. Ge. *Nature Chem.* 2016, advance online publication, doi:10.1038/nchem.2606. This transient directing group is lamely limited to amines containing a-quaternary centers and not compatible with acyclic methylene C—H bonds.

(14) Wang, P.; Farmer, M. E.; Huo, X.; Jain, P.; Shen, P.-X.; Ishoey, M.; Bradner, J. E.; Wisniewski, S. R.; Eastgate, M. D.; Yu, J.-Q. *J. Am. Chem. Soc.* 2016, 138, 9269.

(15) Siliphaivanh, P.; Methot, J.; Lipford, K. A.; Molinari, D.; Sloman, D. L.; Witter, D.; Zhou, H.; Boyce, C.; Huang, X.; Lim, J.; Guerin, D.; Karunakaran, G. B.; Bakshi, R. K.; Liu, Z.; Fu, J.; Wan, Z.; Liu, W.; PCT Int 100050, 2016.

(16) In most cases, directed C(sp³)-H functionalization only applies for amines bearing a-substituent, see ref 7-8. Reduced yields were obtained with amines bearing no a-substituent in ref. 7f, 7g, 7l, 8c, 11 & 13.

(17) For selected examples, see: (a) Wang, J.; Breslin, M. J.; Coleman, P. J.; Duggan, M. E.; Hunt, C. A.; Hutchinson, J. H.; Leu, C.-T.; Rodan, S. B.; Rodan, G. A.; Duong, L. T.; Hartman, G. D. *Bioorg. Med. Chem. Lett.* 2004, 14, 1049. (b) Manley, P. J.; Miller, W. H.; Uzinskas, I. N. PCT Int. 017959, 2001. (c) Nagarajan, S. R.; Khanna, I. K.; Clare, M.; Gasiecki, A.; Rogers, T.; Chen, B.; Russell, M.; Lu, H.-F.; Yi, Y.; Huff, R. M. U.S. Pat. No. 0,092,538, 2004.

All patents and publications referred to herein are incorporated by reference herein to the same extent as if each individual publication was specifically and individually indicated to be incorporated by reference in its entirety.

EXAMPLES

1. General Information 2-hydroxynicotinaldehyde was purchased from Combi-blocks and used directly in the reactions. Amines, solvents and other chemicals were obtained from Sigma-Aldrich, Acros and Alfa Aesar, and used directly without further purification. Analytical thin layer chromatography was performed on 0.25 mm silica gel 60-F254. Visualization was carried out with UV light and Vogel's permanganate. Preparative TLC was performed on 1.0 mm silica gel (Analtech). Columns for flash chromatography (FC) contained silica gel (32-63µ, Dynamic Adsorbents, Inc.). $^1$H NMR spectra were recorded on Bruker AV-400 instrument (400 MHz) or Varian Inova 400 (400 MHz), Bruker DRX-600 instrument (600 MHz). Chemical shifts were quoted in parts per million (ppm) referenced to 0.0 ppm for tetramethylsilane. $^{13}$C NMR spectra were recorded on Bruker DRX-600 instrument (150 MHz), and were fully decoupled by broad band proton decoupling. Chemical shifts were reported in ppm referenced to the center line of a triplet at 77.0 ppm of CDCl3. High-resolution mass spectra (HRMS) were recorded on an Agilent Mass spectrometer using ESI-TOF (electrospray ionization-time of flight).

2. Experimental Section 2.1 Solvent Screening

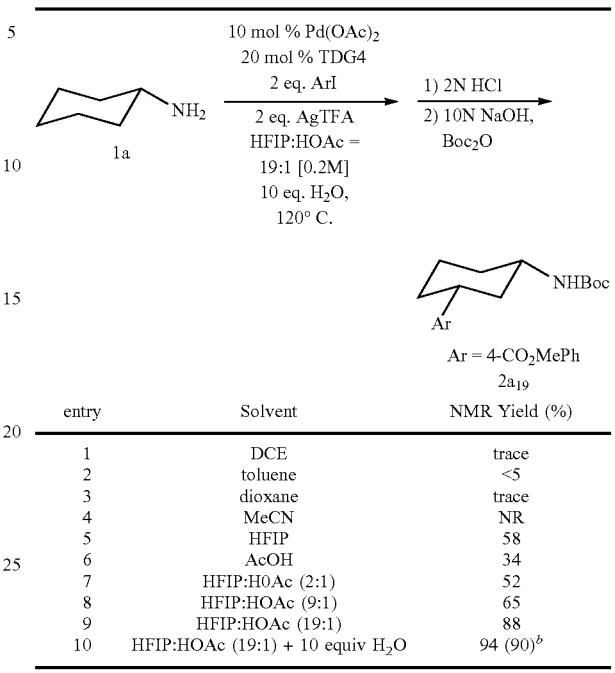

| entry | Solvent | NMR Yield (%) |
|---|---|---|
| 1 | DCE | trace |
| 2 | toluene | <5 |
| 3 | dioxane | trace |
| 4 | MeCN | NR |
| 5 | HFIP | 58 |
| 6 | AcOH | 34 |
| 7 | HFIP:H0Ac (2:1) | 52 |
| 8 | HFIP:HOAc (9:1) | 65 |
| 9 | HFIP:HOAc (19:1) | 88 |
| 10 | HFIP:HOAc (19:1) + 10 equiv H$_2$O | 94 (90)[b] |

[a]Reaction conditions: 1a (0.2 mmol), 4-(CO$_2$Me)Ph-I (2.0 equiv), Pd(OAc)$_2$ (10 mol %), TDG4 (20 mol %), AgTFA (2.0 equiv), solvents (1.0 mL), 120° C., 12 h.
[b]isolated yield.

2.2 General Procedure for Pd-Catalyzed γ-C(sp³)-H Arylation of Free Amines Using a Transient Directing Group To an oven dried microwave tube (5 mL) equipped with a magnetic stir bar was added Pd(OAc)$_2$ (4.5 mg, 0.02 mmol, 10 mol %), transient directing group (TDG4, 4.9 mg, 0.02 mmol, 20 mol %), ArI (0.4 mmol), AgTFA (0.4 mmol) and solvent (HFIP/HOAc=19/1, 1.0 mL), followed by the free amine substrate (0.2 mmol), and H$_2$O (36 uL). The tube was capped and covered with safety shield. Then the mixture was stirred at room temperature for 10 mins before heating to 120° C. for 12 hours under vigorous stirring. Upon completion, the reaction mixture was cooled to room temperature and the dark brown suspension was passed through a pad of Celite and washed with THF (1.0 mL×3). The THF solutions were combined and concentrated under vacuum. Then THF (0.8 mL) and HCl (2 N, 0.8 mL) were added to the residue and the mixture was stirred at rt for 1 h. The mixture was subsequently basified with NaOH (10 M, 0.4 mL) (Checked with pH paper) and Boc$_2$O (4.0 eq.) was added. The brown solution was then vigorously stirred at room temperature for 4 hr. Ethyl Acetate (2.0 mL) was added and well mixed. The top organic layer was separated and passed through a pad of Silica (3 cm). The remaining aqueous layer was further extracted with ethyl acetate (2.0 mL×3). Every time the organic extract was passed through the above pad of Silica. All the organic extracts were collected, combined in a vial and evaporated under reduced pressure and the resulting mixture was purified by prep TLC or flesh column chromatography (Hex/EA=3/1)

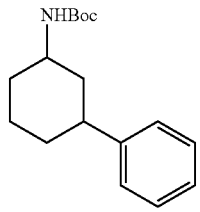 [SMILES: CC(C)(C)OC(=O)NC1CCCC(c2ccccc2)C1]

tert-butyl (3-phenylcyclohexyl)carbamate (2a$_1$)

Following the general procedure, compound 2a$_1$ was obtained as a single diastereomer (cis) and a white solid (47.4 mg, 86% yield) after purification by preparative TLC (eluent: hexane/EtOAc=5/1). $^1$H NMR (600 MHz, CDCl$_3$) δ 7.31-7.26 (m, 2H), 7.21-7.16 (m, 3H), 4.43 (s, 1H), 3.66-3.50 (m, 1H), 2.62 (tt, J=12.3, 3.4 Hz, 1H), 2.19-2.23 (m, 1H), 2.09-2.01 (m, 1H), 1.95-1.82 (m, 2H), 1.47-1.51 (m, 10H), 1.34 (qd, J=12.6, 3.4 Hz, 1H), 1.23 (q, J=12.0 Hz, 1H), 1.10 (qd, J=12.5, 3.8 Hz, 1H). $^{13}$C NMR (151 MHz, CDCl$_3$) δ 155.16, 146.27, 128.38, 126.74, 126.09, 79.11, 50.03, 43.25, 41.43, 33.21, 33.12, 28.42, 25.20. HRMS (ESI-TOF) Calcd for C$_{17}$H$_{25}$NO$_2$Na [M+Na]$^+$: 298.1778; found: 298.1777.

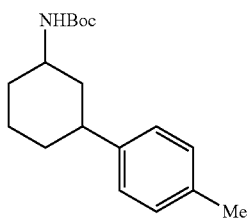 [SMILES: Cc1ccc(C2CCCC(NC(=O)OC(C)(C)C)C2)cc1]

tert-butyl (3-(p-tolyl)cyclohexyl)carbamate (2a$_2$)

Following the general procedure, compound 2a$_2$ was obtained as a single diastereomer (cis) and a white solid (52.6 mg, 91% yield) after purification by preparative TLC (eluent: hexane/EtOAc=5/1). $^1$H NMR (600 MHz, CDCl$_3$) 7.12-7.06 (m, 4H), 4.43 (d, J=8.8 Hz, 1H), 3.57 (s, 1H), 2.59 (tt, J=12.4, 3.4 Hz, 1H), 2.31 (s, 3H), 2.21-2.12 (m, 1H), 2.04 (dddd, J=9.0, 5.5, 3.7, 1.8 Hz, 1H), 1.91-1.80 (m, 2H), 1.55-1.46 (m, 1H), 1.45 (s, 9H), 1.32 (qd, J=12.8, 3.5 Hz, 1H), 1.21 (q, J=12.1 Hz, 1H), 1.08 (qd, J=12.5, 3.8 Hz, 1H). $^{13}$C NMR (151 MHz, CDCl$_3$) δ 155.15, 143.33, 135.53, 129.05, 126.59, 79.09, 50.05, 42.81, 41.52, 33.23, 28.42, 25.20, 20.96. HRMS (ESI-TOF) Calcd C$_{18}$H$_{27}$NO$_2$Na [M+Na]$^+$: 312.1934; found: 312.1927

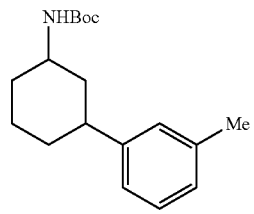 [SMILES: Cc1cccc(C2CCCC(NC(=O)OC(C)(C)C)C2)c1]

tert-butyl (3-(m-tolyl)cyclohexyl)carbamate (2a$_3$)

Following the general procedure, compound 2a$_3$ was obtained as a single diastereomer (cis) and a white solid (52.7 mg, 91% yield) after purification by preparative TLC (eluent: hexane/EtOAc=5/1). $^1$H NMR (600 MHz, CDCl$_3$) δ 7.17 (t, J=7.8 Hz, 1H), 7.02-6.96 (m, 3H), 4.56-4.37 (m, 1H), 3.57 (d, J=11.1 Hz, 1H), 2.58 (tt, J=12.3, 3.3 Hz, 1H), 2.32 (s, 3H), 2.18 (d, J=12.4 Hz, 1H), 2.04 (dddt, J=10.6, 5.6, 3.7, 1.9 Hz, 1H), 1.91-1.81 (m, 2H), 1.48-1.51 (m, 11H), 1.33 (qd, J=12.8, 3.6 Hz, 1H), 1.22 (q, J=12.0 Hz, 1H), 1.09 (qd, J=12.5, 3.9 Hz, 1H). $^{13}$C NMR (151 MHz, CDCl$_3$) δ 155.16, 145.25, 137.86, 128.27, 127.59, 126.83, 123.72, 79.07, 50.04, 43.19, 41.45, 33.21, 33.11, 28.44, 25.21, 21.46. HRMS (ESI-TOF) Calcd C$_{16}$H$_{27}$NO$_2$Na [M+Na]$^+$: 312.1934; found: 312.1930.

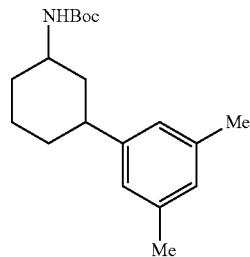 [SMILES: Cc1cc(C)cc(C2CCCC(NC(=O)OC(C)(C)C)C2)c1]

tert-butyl (3-(3,5-dimethylphenyl)cyclohexyl)carbamate (2a$_4$)

Following the general procedure, compound 2a$_4$ was obtained as a single diastereomer (cis) and a white solid (53.4 mg, 88% yield) after purification by preparative TLC (eluent: hexane/EtOAc=5/1). $^1$H NMR (600 MHz, CDCl$_3$) δ 6.84-6.79 (m, 3H), 4.42 (s, 1H), 3.56 (s, 1H), 2.55 (tt, J=12.5, 3.5 Hz, 1H), 2.28 (s, 6H), 2.19-2.14 (m, 1H), 2.08-2.00 (m, 1H), 1.91-1.80 (m, 2H), 1.52-1.45 (m, 1H), 1.43 (s, 9H), 1.33 (qd, J=12.7, 3.5 Hz, 1H), 1.21 (q, J=12.1 Hz, 1H), 1.08 (qd, J=12.5, 3.9 Hz, 1H). $^{13}$C NMR (151 MHz, CDCl$_3$) δ 155.16, 146.29, 137.80, 127.74, 124.60, 79.07, 50.07, 43.13, 41.49, 33.24, 33.11, 28.44, 25.22, 21.33. HRMS (ESI-TOF) Calcd for C$_{19}$H$_{29}$NO$_2$Na [M+Na]$^+$: 326.2091; found: 326.2084.

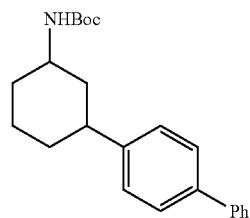 [SMILES: CC(C)(C)OC(=O)NC1CCCC(c2ccc(-c3ccccc3)cc2)C1]

tert-butyl (3-([1,1'-biphenyl]-4-yl)cyclohexyl)carbamate (2a₅)

Following the general procedure, compound 2a₅ was obtained as a single diastereomer (cis) and a white solid (58.3 mg, 83% yield) after purification by preparative TLC (eluent: hexane/EtOAc=5/1). ¹H NMR (500 MHz, CDCl3) δ 7.57 (dd, J=8.2, 1.4 Hz, 2H), 7.52 (d, J=8.0 Hz, 2H), 7.41 (t, J=7.6 Hz, 2H), 7.34-7.29 (m, 1H), 7.26 (d, J=8.1 Hz, 2H), 4.45 (d, J=7.7 Hz, 1H), 3.60 (s, 1H), 2.67 (tt, J=12.3, 3.3 Hz, 1H), 2.23 (d, J=12.3 Hz, 1H), 2.10-2.02 (m, 1H), 1.90 (tq, J=9.5, 3.4 Hz, 2H), 1.57-1.48 (m, 1H), 1.44 (s, 9H), 1.41-1.32 (m, 1H), 1.26 (q, J=12.1 Hz, 1H), 1.11 (qd, J=12.5, 3.7 Hz, 1H). ¹³C NMR (151 MHz, CDCl₃) δ 155.16, 145.38, 141.01, 139.04, 128.69, 127.16, 127.11, 127.01, 126.99, 79.13, 50.02, 42.89, 41.42, 33.19, 33.11, 28.43, 25.20. HRMS (ESI-TOF) Calcd for $C_{23}H_{29}NO_2Na$ [M+Na]⁺: 374.2091; found: 374.2086.

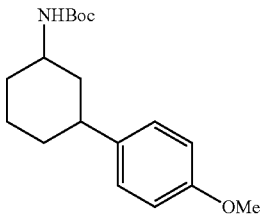 [SMILES: COc1ccc(C2CCCC(NC(=O)OC(C)(C)C)C2)cc1]

tert-butyl (3-(4-methoxyphenyl)cyclohexyl)carbamate (2a₆)

Following the general procedure, compound 2a₆ was obtained as a single diastereomer (cis) and a white solid (48.9 mg, 80% yield) after purification by preparative TLC (eluent: hexane/EtOAc=5/1). ¹H NMR (600 MHz, CDCl₃) δ 7.13-7.07 (m, 2H), 6.86-6.80 (m, 2H), 4.45 (s, 1H), 3.78 (s, 3H), 3.64-3.49 (m, 1H), 2.57 (tt, J=12.3, 3.5 Hz, 1H), 2.16 (d, J=12.4 Hz, 1H), 2.03 (dtd, J=11.8, 3.8, 1.8 Hz, 1H), 1.91-1.78 (m, 2H), 1.55-1.46 (m, 1H), 1.43 (s, 9H), 1.30 (qd, J=12.9, 3.7 Hz, 1H), 1.18 (q, J=12.1 Hz, 1H), 1.08 (qd, J=12.5, 3.8 Hz, 1H). ¹³C NMR (151 MHz, CDCl₃) δ 157.85, 155.16, 138.54, 127.57, 113.74, 79.08, 55.23, 50.04, 42.36, 41.69, 33.36, 33.19, 28.42, 25.18. HRMS (ESI-TOF) Calcd for $C_{18}H_{27}NO_3Na$ [M+Na]⁺: 328.1883; found: 328.1882.

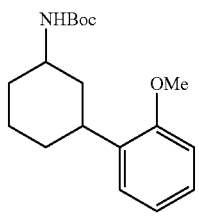 [SMILES: COc1ccccc1C1CCCC(NC(=O)OC(C)(C)C)C1]

tert-butyl (3-(2-methoxyphenyl)cyclohexyl)carbamate (2a₇)

Following the general procedure, compound 2a₇ was obtained as a single diastereomer (cis) and a white solid (39.7 mg, 65% yield) after purification by preparative TLC (eluent: hexane/EtOAc=5/1). ¹H NMR (600 MHz, CDCl₃) δ 7.23-7.17 (m, 2H), 6.78 (dt, J=7.5, 1.3 Hz, 1H), 6.73 (dt, J=7.6, 2.0 Hz, 1H), 4.44 (s, 1H), 3.79 (s, 3H), 3.65-3.49 (m, 1H), 2.60 (tt, J=12.3, 3.4 Hz, 1H), 2.19 (d, J=12.3 Hz, 1H), 2.04 (dqt, J=10.8, 3.5, 1.7 Hz, 1H), 1.93-1.81 (m, 2H), 1.53-1.40 (m, 10H), 1.33 (qd, J=12.6, 3.4 Hz, 1H), 1.22 (q, J=12.0 Hz, 1H), 1.14-1.04 (m, 1H). ¹³C NMR (151 MHz, CDCl₃) δ 156.69, 155.15, 134.45, 126.82, 126.48, 120.48, 110.46, 78.99, 55.31, 50.11, 39.95, 35.69, 33.57, 31.84, 28.44, 25.29. HRMS (ESI-TOF) Calcd for $C_{18}H_{27}NO_3Na$ [M+Na]⁺: 328.1883; found: 328.1882.

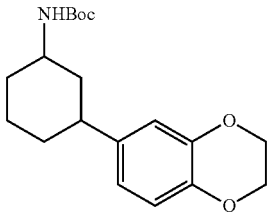 [SMILES: CC(C)(C)OC(=O)NC1CCCC(c2ccc3c(c2)OCCO3)C1]

tert-butyl (3-(2,3-dihydrobenzo[b][1,4]dioxin-6-yl)cyclohexyl)carbamate (2a₈)

Following the general procedure, compound 2a₈ was obtained as a single diastereomer (cis) and a white solid (49.6 mg, 75% yield) after purification by preparative TLC (eluent: hexane/EtOAc=5/1). ¹H NMR (600 MHz, CDCl₃) δ 6.77 (d, J=8.2 Hz, 1H), 6.69 (d, J=2.1 Hz, 1H), 6.66 (dd, J=8.3, 2.1 Hz, 1H), 4.43 (d, J=8.2 Hz, 1H), 4.25-4.21 (m, 4H), 3.55 (d, J=11.1 Hz, 1H), 2.52 (tt, J=12.4, 3.3 Hz, 1H), 2.15 (d, J=12.4 Hz, 1H), 2.05-1.99 (m, 1H), 1.89-1.78 (m, 2H), 1.50-1.45 (m, 1H), 1.43 (s, 9H), 1.27 (qd, J=12.8, 3.6 Hz, 1H), 1.16 (q, J=12.0 Hz, 1H), 1.07 (qd, J=12.5, 3.9 Hz, 1H). ¹³C NMR (151 MHz, CDCl₃) δ 155.15, 143.26, 141.71, 139.84, 119.68, 116.99 115.30, 77.24, 64.41, 64.31, 49.98, 42.47, 41.56, 33.28, 33.18, 28.42, 25.13. HRMS (ESI-TOF) Calcd for $C_{19}H_{27}NO_4Na$ [M+Na]⁺: 356.1832; found: 356.1826.

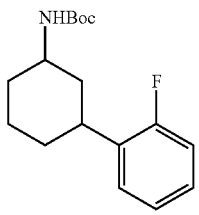 [SMILES: CC(C)(C)OC(=O)NC1CCCC(c2ccccc2F)C1]

tert-butyl (3-(2-fluorophenyl)cyclohexyl)carbamate (2a₉)

Following the general procedure, compound 2a₉ was obtained as a single diastereomer (cis) and a white solid (36.9 mg, 63% yield) after purification by preparative TLC (eluent: hexane/EtOAc=5/1). ¹H NMR (600 MHz, CDCl3) δ 7.21-7.13 (m, 2H), 7.06 (t, J=7.2 Hz, 1H), 6.99 (ddd, J=9.5, 8.3, 1.2 Hz, 1H), 4.55-4.36 (m, 1H), 3.59 (s, 1H), 2.95 (tt, J=12.3, 3.4 Hz, 1H), 2.16 (dtt, J=11.8, 3.7, 2.0 Hz, 1H), 2.09-2.02 (m, 1H), 1.89 (dp, J=13.5, 3.4 Hz, 1H), 1.83 (dtd, J=13.0, 3.4, 1.7 Hz, 1H), 1.51 (qt, J=13.3, 3.5 Hz, 1H), 1.44 (s, 9H), 1.37 (qd, J=12.7, 3.5 Hz, 1H), 1.31 (q, J=11.9, 8.8 Hz, 1H), 1.12 (qd, J=12.6, 3.9 Hz, 1H). ¹³C NMR (151 MHz, CDCl3) δ 160.92, 159.30, 154.66, 132.30 (d, J=14.3

Hz), 127.27, 126.95 (d, J=8.5 Hz), 123.57 (d, J=3.7 Hz), 114.93 (d, J=22.3 Hz), 78.66, 49.45, 39.13, 35.98, 32.76, 27.96, 24.68. $^{19}$F NMR (400 MHz, CDCl3) δ −119.06 (s). RMS (ESI-TOF) Calcd for $C_{17}H_{24}FNO_2Na$ [M+Na]$^+$: 316.1683; found: 316.1679.

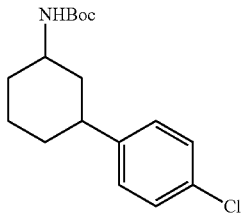 [SMILES: CC(C)(C)OC(=O)NC1CCCC(c2ccc(Cl)cc2)C1]

tert-butyl (3-(4-chlorophenyl)cyclohexyl)carbamate
($2a_{10}$)

Following the general procedure, compound $2a_{10}$ was obtained as a single diastereomer (cis) and a white solid (45.2 mg, 73% yield) after purification by preparative TLC (eluent: hexane/EtOAc=5/1). $^1$H NMR (600 MHz, CDCl$_3$) δ 7.24 (d, J=8.4 Hz, 2H), 7.11 (d, J=8.5 Hz, 2H), 4.45 (s, 1H), 3.57 (s, 1H), 2.60 (tt, J=12.3, 3.4 Hz, 1H), 2.17 (d, J=12.3 Hz, 1H), 2.03 (dtq, J=10.7, 3.5, 1.8 Hz, 1H), 1.89 (dp, J=13.6, 3.4 Hz, 1H), 1.82 (dpd, J=10.0, 3.3, 2.1, 1.4 Hz, 1H), 1.49 (tt, J=13.3, 3.5 Hz, 1H), 1.43 (s, 9H), 1.34-1.26 (m, 1H), 1.18 (q, J=12.1 Hz, 1H), 1.09 (qd, J=12.6, 3.9 Hz, 1H). $^{13}$C NMR (151 MHz, CDCl$_3$) δ 155.14, 144.69, 131.66, 128.46, 128.10, 79.19, 49.92, 42.64, 41.34, 33.10, 33.07, 28.42, 25.11. RMS (ESI-TOF) Calcd for $C_{17}H_{24}ClNO_2Na$ [M+Na]$^+$: 332.1388; found: 332.1382.

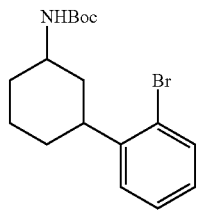 [SMILES: CC(C)(C)OC(=O)NC1CCCC(c2ccccc2Br)C1]

tert butyl (3-(2-bromophenyl)cyclohexyl)carbamate
($2a_{11}$)

Following the general procedure, compound $2a_{11}$ was obtained as a single diastereomer (cis) and a white solid (43.1 mg, 61% yield) after purification by preparative TLC (eluent: nexane/EtOAc=5/1). $^1$H NMR (600 MHz, CDCl$_3$) δ 7.53 (dd, J=8.0, 1.3 Hz, 1H), 7.28-7.23 (m, 1H), 7.21 (dd, J=7.8, 1.8 Hz, 1H), 7.04 (td, J=7.6, 1.8 Hz, 1H), 4.44 (s, 1H), 3.62 (s, 1H), 3.10 (t, J=12.2 Hz, 1H), 2.20 (dtt, J=11.8, 3.8, 2.1 Hz, 1H), 2.08 (d, J=12.6 Hz, 1H), 1.94-1.84 (m, 2H), 1.54 (qt, J=13.8, 3.7 Hz, 1H), 1.44 (s, 9H), 1.31-1.17 (m, 2H), 1.11 (qd, J=12.6, 3.8 Hz, 1H). $^{13}$C NMR (151 MHz, CDCl$_3$) δ 154.63, 144.20, 132.49, 127.10, 127.06, 126.66, 123.97, 78.68, 49.45, 41.44, 39.30, 32.83, 31.74, 27.98, 24.64. HRMS (ESI-TOF) Calcd for $C_{17}H_{24}BrNO_2Na$ [M+Na]$^+$: 376.0883; found: 334.0881.

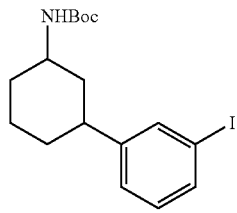 [SMILES: CC(C)(C)OC(=O)NC1CCCC(c2cccc(I)c2)C1]

tert-butyl (3-(3-iodophenyl)cyclohexyl)carbamate
($2a_{12}$)

Following the general procedure, compound $2a_{12}$ was obtained as a single diastereomer (cis) and a white solid (48.9 mg, 61% yield) after purification by preparative TLC (eluent: hexane/EtOAc=5/1). $^1$H NMR (400 MHz, CDCl$_3$) δ 7.54 (d, J=1.8 Hz, 1H), 7.52 (dt, J=7.7, 1.4 Hz, 1H), 7.14 (dt, J=7.7, 1.3 Hz, 1H), 7.01 (t, J=7.8 Hz, 1H), 4.44 (d, J=8.1 Hz, 1H), 3.65-3.49 (m, 1H), 2.56 (tt, J=12.4, 3.4 Hz, 1H), 2.18 (d, J=12.3 Hz, 1H), 2.07-1.99 (m, 1H), 1.89 (dp, J=13.6, 3.4 Hz, 1H), 1.85-1.81 (m, 1H), 1.48 (dt, J=13.7, 3.7 Hz, 1H), 1.44 (s, 9H), 1.34-1.27 (m, 1H), 1.19 (q, J=12.1 Hz, 1H), 1.09 (qd, J=12.6, 3.9 Hz, 1H). $^{13}$C NMR (151 MHz, CDCl$_3$) δ 155.13, 148.67, 135.85, 130.17, 128.38, 126.20, 94.56, 79.20, 49.88, 43.24, 42.87, 41.19, 33.03, 28.42, 25.08. HRMS (ESI-TOF) Calcd for $C_{17}H_{24}INO_2Na$ [M+Na]$^+$: 424.0744; found: 424.0746.

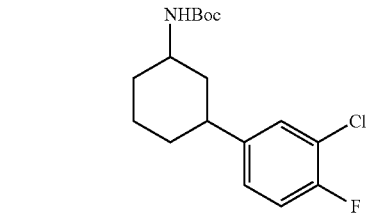 [SMILES: CC(C)(C)OC(=O)NC1CCCC(c2ccc(F)c(Cl)c2)C1]

tert-butyl (3-(3-chloro-4-fluorophenyl)cyclohexyl)
carbamate ($2a_{13}$)

Following the general procedure, compound $2a_{13}$ was obtained as a single diastereomer (cis) and a white solid (48.4 mg, 74% yield) after purification by preparative TLC (eluent: hexane/EtOAc=4/1). $^1$H NMR (600 MHz, CDCl$_3$) δ 7.23-7.18 (m, 1H), 7.07-7.01 (m, 2H), 4.45 (d, J=8.1 Hz, 1H), 3.57 (s, 1H), 2.59 (tt, J=12.3, 3.3 Hz, 1H), 2.18 (d, J=12.3 Hz, 1H), 2.03 (dtt, J=10.4, 3.6, 1.9 Hz, 1H), 1.90 (dp, J=13.6, 3.4 Hz, 1H), 1.83 (dtt, J=11.8, 3.5, 1.8 Hz, 1H), 1.49 (tt, J=13.4, 3.6 Hz, 1H), 1.44 (s, 9H), 1.32-1.24 (m, 1H), 1.17 (q, J=12.0 Hz, 1H), 1.10 (qd, J=12.6, 3.9 Hz, 1H). $^{13}$C NMR (151 MHz, CDCl$_3$) δ 157.31, 155.68, 155.15, 143.25 (d, J=3.2 Hz), 128.70, 126.43 (d, J=6.8 Hz), 120.57 (d, J=17.5 Hz), 116.32 (d, J=20.6 Hz), 79.26, 49.84, 42.33, 41.35, 33.15, 32.95, 28.41, 25.03. $^{19}$F NMR (400 MHz, CDCl3) δ −119.9 (s). HRMS (ESI-TOF) Calcd for $C_{17}H_{23}ClFNO_2Na$ [M+Na]$^+$: 350.1294; found: 350.1288.

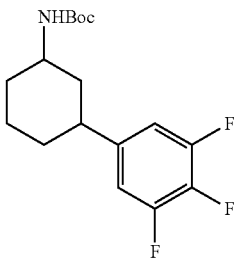 [SMILES: CC(C)(C)OC(=O)NC1CCCC(c2cc(F)c(F)c(F)c2)C1]

tert-butyl
(3-(3,4,5-trifluorophenyl)cyclohexyl)carbamate
(2a$_{14}$)

Following the general procedure, compound 2a$_{14}$ was obtained as a single diastereomer (cis) and a white solid (34.2 mg, 52% yield) after purification by preparative TLC (eluent: hexane/EtOAc=3/1). $^1$H NMR (500 MHz, CDCl$_3$) δ 6.82-6.75 (m, 2H), 4.51-4.32 (m, 1H), 3.56 (s, 1H), 2.57 (tt, J=12.3, 3.4 Hz, 1H), 2.19 (d, J=12.2 Hz, 1H), 2.05-2.00 (m, 1H), 1.91 (dp, J=13.6, 3.4 Hz, 1H), 1.82 (dtd, J=11.6, 3.2, 1.6 Hz, 1H), 1.49 (ddd, J=13.4, 9.7, 3.6 Hz, 1H), 1.44 (s, 9H), 1.24 (qd, J=12.9, 3.8 Hz, 1H), 1.18-1.04 (m, 2H). $^{13}$C NMR (151 MHz, CDCl$_3$) δ 154.65, 151.44 (dd, J=9.8, 4.2 Hz), 149.79 (dd, J=9.7, 4.0 Hz), 141.97 (q, J=6.4 Hz), 138.39 (t, J=15.4 Hz), 136.69 (d, J=15.5 Hz), 110.12 (dd, J=16.4, 4.1 Hz), 78.88, 67.51, 49.24, 42.01, 40.6, 32.46, 27.94, 24.43. $^{19}$F NMR (400 MHz, CDCl$_3$) δ −135.27 (d, J=20.8 Hz), −164.48 (t, J=20.7 Hz). HRMS (ESI-TOF) Calcd for C$_{17}$H$_{22}$F$_3$NO$_2$ [M+H]$^+$: 330.1675; found: 330.1671.

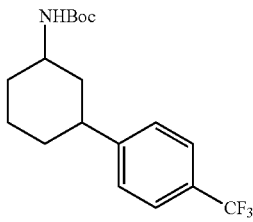

tert-butyl (3-(4-(trifluoromethyl)phenyl)cyclohexyl)carbamate (2a$_{15}$)

Following the general procedure, compound 2a$_{15}$ was obtained as a single diastereomer (cis) and a white solid (56.9 mg, 83% yield) after purification by preparative TLC (eluent: hexane/EtOAc=4/1). $^1$H NMR (400 MHz, CDCl$_3$) δ 7.54 (d, J=8.1 Hz, 2H), 7.29 (d, J=8.0 Hz, 2H), 4.48 (d, J=8.3 Hz, 1H), 3.60 (d, J=11.0 Hz, 1H), 2.69 (tt, J=12.3, 3.4 Hz, 1H), 2.21 (d, J=12.3 Hz, 1H), 2.05 (dtt, J=12.5, 4.0, 2.0 Hz, 1H), 1.92 (dp, J=13.5, 3.4 Hz, 1H), 1.85 (dtt, J=11.7, 3.5, 1.9 Hz, 1H), 1.51 (qt, J=13.2, 3.7 Hz, 1H), 1.44 (s, 9H), 1.35 (qd, J=12.8, 3.6 Hz, 1H), 1.23 (q, J=12.1 Hz, 1H), 1.13 (qd, J=12.6, 3.9 Hz, 1H). $^{13}$C NMR (151 MHz, CDCl$_3$) δ 154.69, 149.73, 127.96 (q, J=32.4 Hz), 126.63, 124.86 (q, J=3.7 Hz), 122.93, 78.78, 49.42, 42.66, 40.63, 32.54, 32.45, 27.94, 24.63. $^{19}$F NMR (400 MHz, CDCl$_3$) δ −62.61 (s), HRMS (ESI-TOF) Calcd for C$_{18}$H$_{24}$F$_3$NO$_2$Na [M+Na]$^+$: 366.1651; found: 366.1648.

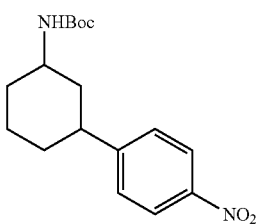 [SMILES: CC(C)(C)OC(=O)NC1CCCC(c2ccc([N+](=O)[O-])cc2)C1]

tert-butyl (3-(4-nitrophenyl)cyclohexyl)carbamate
(2a$_{16}$)

Following the general procedure, compound 2a$_{16}$ was obtained as a single diastereomer (cis) and a white solid (46.7 mg, 73% yield) after purificatim by preparative TLC (eluent: hexane/EtOAc=4/1). $^1$H NMR (600 MHz, CDCl$_3$) δ 8.15 (d, J=8.7 Hz, 2H), 7.37-7.32 (m, 2H), 4.49 (d, J=8.1 Hz, 1H), 3.61 (s, 1H), 2.75 (tt, J=12.3, 3.4 Hz, 1H), 2.23 (d, J=12.3 Hz, 1H), 2.06 (ddq, J=12.5, 3.8, 1.9 Hz, 1H), 1.94 (dp, J=13.6, 3.4 Hz, 1H), 1.87 (dtd, J=15.1, 3.6, 2.0 Hz, 1H), 1.53 (qt, J=13.3, 3.6 Hz, 1H), 1.44 (s, 9H), 1.36 (qd, J=12.8, 3.6 Hz, 1H), 1.25 (q, J=12.1 Hz, 1H), 1.15 (qd, J=12.6, 3.9 Hz, 1H). $^{13}$C NMR (151 MHz, CDCl$_3$) δ 155.14, 153.76, 146.44, 127.62, 123.75, 79.34, 49.78, 43.22, 40.87, 32.87, 32.81, 28.41, 25.04. HRMS (ESI-TOF) Calcd or C$_{17}$H$_{24}$N$_2$O$_4$Na [M+Na]$^+$: 343.1628; found: 343.1630.

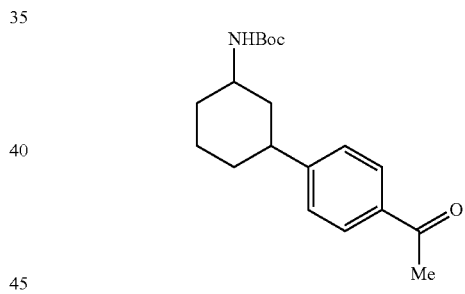

tert-butyl (3-(4-acetylphenyl)cyclohexyl)carbamate
(2a$_{17}$)

Following the general procedure, compound 2a$_{17}$ was obtained as a single diastereomer (cis) and a white solid (50.7 mg, 80% yield) after purification by preparative TLC (eluent: hexane/EtOAc=4/1). $^1$H NMR (600 MHz, CDCl$_3$) δ 7.89 (d, J=8.3 Hz, 2H), 7.28 (d, J=8.3 Hz, 2H), 4.47 (s, 1H), 3.60 (s, 1H), 2.74-2.66 (m, 1H), 2.58 (s, 3H), 2.21 (d, J=12.3 Hz, 1H), 2.09-2.03 (m, 1H), 1.92 (dp, J=13.5, 3.4 Hz, 1H), 1.86 (dtt, J=12.2, 4.2, 2.1 Hz, 1H), 1.51 (qt, J=13.2, 3.5 Hz, 1H), 1.44 (s, 9H), 1.36 (qd, J=12.7, 3.5 Hz, 1H), 1.25 (q, J=12.1 Hz, 1H), 1.13 (qd, J=12.6, 3.9 Hz, 1H). $^{13}$C NMR (151 MHz, CDCl$_3$) δ 197.35, 154.69, 151.37, 134.85, 128.16, 126.53, 78.78, 49.42, 42.85, 40.52, 32.58, 32.39, 27.95, 26.10, 24.65. HRMS (ESI-TOF) Calcd for C$_{19}$H$_{27}$NO$_3$Na [M+Na]$^+$: 340.1883; found: 340.1879.

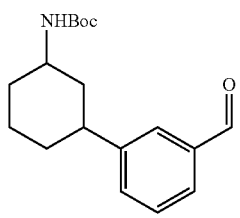 [SMILES: CC(C)(C)OC(=O)NC1CCCC(c2cccc(C=O)c2)C1]

tert-butyl (3-(3-formylphenyl)cyclohexyl)carbamate (2a$_{18}$)

Following the general procedure, compound 2a$_{18}$ was obtained as a single diastereomer (cis) and a white solid (38.2 mg, 63% yield) after purification by preparative TLC (eluent: hexane/EtOAc=2/1). $^1$H NMR (500 MHz, CDCl$_3$) δ 9.99 (s, 1H), 7.71 (ddd, J=8.6, 4.5, 2.2 Hz, 2H), 7.50-7.41 (m, 2H), 4.50 (d, J=8.7 Hz, 1H), 3.69-3.53 (m, 1H), 2.72 (tt, J=12.4, 3.3 Hz, 1H), 2.24 (d, J=12.3 Hz, 1H), 2.06 (ddt, J=8.6, 5.8, 3.0 Hz, 1H), 1.97-1.84 (m, 2H), 1.57-1.48 (m, 1H), 1.44 (s, 9H), 1.40-1.33 (m, 1H), 1.28 (qd, J=11.6, 11.2, 3.2 Hz, 1H), 1.14 (qd, J=12.5, 3.8 Hz, 1H). $^{13}$C NMR (151 MHz, CDCl$_3$) δ 192.52, 155.17, 147.30, 136.62, 133.37, 129.08, 128.06, 127.48, 79.23, 49.90, 42.93, 41.14, 33.04, 32.99, 28.42, 25.11. HRMS (ESI-TOF) Calcd for C$_{18}$H$_{25}$NO$_3$Na [M+Na]$^+$: 326.1727; found: 326.1725.

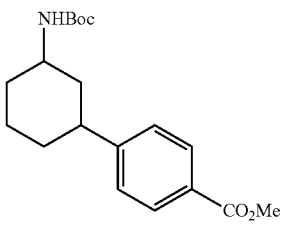 [SMILES: COC(=O)c1ccc(C2CCCC(NC(=O)OC(C)(C)C)C2)cc1]

methyl 4-(3-((tert-butoxycarbonyl)amino)cyclohexyl)benzoate (2a$_{19}$)

Following the general procedure, compound 2a$_{19}$ was obtained as a single diastereomer (cis) and a white solid (59.9 mg, 90% yield) after purification by preparative TLC (eluent: hexane/EtOAc=5/1). $^1$H NMR (400 MHz, CDCl$_3$) δ 7.98-7.93 (m, 2H), 7.26-7.24 (m, 2H), 4.47 (s, 1H), 3.90 (s, 3H), 3.59 (s, 1H), 2.69 (tt, J=12.2, 3.4 Hz, 1H), 2.20 (d, J=12.3 Hz, 1H), 2.05 (dtd, J=14.1, 3.7, 1.9 Hz, 1H), 1.95-1.82 (m, 2H), 1.54-1.47 (m, 1H), 1.43 (s, 9H), 1.35 (qd, J=12.8, 3.6 Hz, 1H), 1.24 (q, J=12.1 Hz, 1H), 1.12 (qd, J=12.5, 3.8 Hz, 1H). $^{13}$C NMR (151 MHz, CDCl$_3$) δ 167.07, 155.15, 151.55, 129.79, 128.08, 126.81, 79.22, 51.98, 49.90, 43.32, 41.02, 33.07, 32.88, 28.42, 25.12. HRMS (ESI-TOF) Calcd for C$_{19}$H$_{27}$NO$_4$Na [M+Na]$^+$: 356.1832; found: 356.1833. The stereochernistiy was determined by 2D NOE analysis.

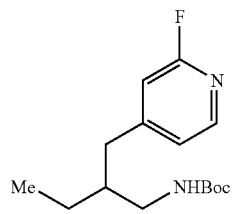 [SMILES: CCC(CNC(=O)OC(C)(C)C)Cc1ccnc(F)c1]

tert-butyl (2-((2-fluoropyridin-4-yl)methyl)butyl)carbamate (2b$_1$)

Following the general procedure, compound 2b$_1$ was obtained as a white solid (37.2 mg, 66% yield) after purification by preparative TLC (eluent: hexane/EtOAc=2/1). $^1$H NMR (400 MHz, CDCl$_3$) δ 8.10 (d, J=5.1 Hz, 1H), 7.00 (d, J=5.1 Hz, 1H), 6.75 (s, 1H), 4.56 (s, 1H), 3.10 (ddt, J=51.0, 13.6, 6.2 Hz, 2H), 2.68-2.54 (m, 2H), 1.82 (q, J=6.6 Hz, 1H), 1.43 (s, 9H), 1.33 (p, J=7.3 Hz, 2H), 0.93 (t, J=7.4 Hz, 3H). $^{13}$C NMR (151 MHz, CDCl$_3$) 164.87, 163.29, 156.05, 147.33 (d, J=15.4 Hz), 122.20 (d, J=3.8 Hz), 109.76 (d, J=36.3 Hz), 79.39, 43.22, 41.29, 37.42, 28.38, 23.92, 10.87. $^{19}$F NMR (400 MHz, CDCl$_3$) δ −69.39 (s). HRMS (ESI-TOF) Calcd for C$_{15}$H$_{24}$FN$_2$O$_2$ [M+H]$^+$: 283.1816; found: 283.1810.

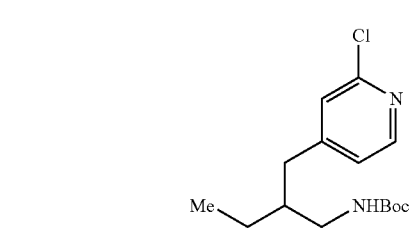 [SMILES: CCC(CNC(=O)OC(C)(C)C)Cc1ccnc(Br)c1]

tert-butyl (2-((2-chloropyridin-4-yl)methyl)butyl)carbamate (2b$_2$)

Following the general procedure, compound 2b$_2$ was obtained as a white solid (41.1 mg, 69% yield) after putification by preparative TLC (eluent: hexane/EtOAc=2/1). $^1$H NMR (500 MHz, CDCl$_3$) δ 8.27 (dd, J=5.2, 1.2 Hz, 1H), 7.15 (s, 1H), 7.05 (d, J=5.1 Hz, 1H), 4.55 (s, 1H), 3.10 (ddt, J=55.6, 13.4, 6.2 Hz, 2H), 2.56 (ddd, J=49.9, 13.9, 7.0 Hz, 2H), 1.80 (dd, J=13.4, 6.8 Hz, 1H), 1.44 (s, 9H), 1.32 (p, J=7.2 Hz, 2H), 0.92 (td, J=7.4, 1.1 Hz, 3H). $^{13}$C NMR (151 MHz, CDCl$_3$) δ 155.56, 152.96, 151.17, 148.99, 124.28, 122.81, 78.93, 42.72, 40.84, 36.80, 27.92, 23.43, 10.40. HRMS (ESI-TOF) Calcd for C$_{15}$H$_{24}$ClN$_2$O$_2$ [M+H]$^+$: 299.1521; found: 299.1518.

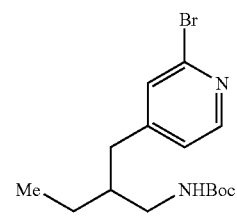

tert-butyl (2((2-bromopyridin-4-yl)methyl)butyl) carbamate (2b₃)

Following the general procedure, compound 2b₃ was obtained as a white solid (38.4 mg, 56% yield) after purification by preparative TLC (eluent: hexane/EtOAc=2/1). ¹H NMR (400 MHz, CDCl₃) 8.25 (d, J=5.1 Hz, 1H), 7.31 (s, 1H), 7.08 (d, J=5.0 Hz, 1H), 4.56 (s, 1H), 3.10 (ddt, J=57.4, 14.3, 6.1 Hz, 2H), 2.55 (ddd, J=52.2, 13.9, 7.0 Hz, 2H), 1.82-1.76 (m, 1H), 1.44 (s, 9H), 1.32 (p, J=7.2 Hz, 2H), 0.92 (t, J=7.5 Hz, 3H). ¹³C NMR (151 MHz, CDCl₃) ¹³C NMR (151 MHz, CDCl₃) δ 156.03, 153.21, 149.88, 142.43, 128.56, 123.66, 79.41, 43.17, 41.32, 37.19, 28.39, 23.89, 10.86. HRMS (ESI-TOF) Calcd for $C_{15}H_{24}BrN_2O_2$ [M+H]⁺: 343.1016; found: 343.1016.

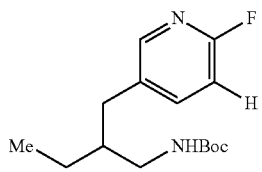 [SMILES: CCC(CNC(=O)OC(C)(C)C)Cc1ccc(F)nc1]

tert-butyl (2-((6-fluoropyridin-3yl)methyl)butyl) carbamate (2b₄)

Following the general procedure, compound 2b₄ was obtained as a white solid (37.8 mg, 67% yield) after purification by preparative TLC (eluent: hexane/EtOAc=2/1). ¹H NMR (400 MHz, CDCl₃) δ 8.03-7.99 (m, 1H), 7.60 (dt, J=8.4, 4.3 Hz, 1H), 6.86 (dd, J=8.4, 2.9 Hz, 1H), 4.53 (s, 1H), 3.09 (ddd, J=35.8, 14.5, 7.9 Hz, 2H), 2.63-2.50 (m, 2H), 1.77-1.71 (m, 1H), 1.44 (s, 9H), 1.35-1.28 (m, 2H), 0.92 (t, J=7.5 Hz, 3H). ¹³C NMR (151 MHz, CDCl₃) 163.16, 161.59, 156.05, 147.55 (d, J=14.2 Hz), 141.58 (d, J=7.6 Hz), 133.45 (d, J=4.4 Hz), 109.09 (d, J=37.3 Hz), 79.34, 43.00, 41.77, 34.07, 28.40, 23.68. ¹⁹F NMR (400 MHz, CDCl₃) δ −72.34 (s). HRMS (ESI-TOF) Calcd for $C_{15}H_{24}FN_2O_2$ [M+H]⁺: 283.1816; found: 283.1817.

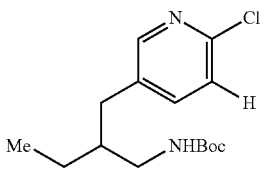 [SMILES: CCC(CNC(=O)OC(C)(C)C)Cc1ccc(Cl)nc1]

tert-butyl (2-((6-chloropyridin-3-yl)methyl)butyl) carbamate (2b₅)

Following the general procedure, compound 2b₅ was obtained as a white solid (35.8 mg, 60% yield) after purification by preparative TLC (eluent: hexane/EtOAc=2/1). ¹H NMR (400 MHz, CDCl₃) δ 8.19 (d, J=2.4 Hz, 1H), 7.53-7.42 (m, 1H), 7.25 (d, J=8.1 Hz, 1H), 4.55 (s, 1H), 3.09 (ddt, J=44.7, 13.8, 6.0 Hz, 2H), 2.59 (dd, J=14.1, 6.8 Hz, 1H), 2.52 (dd, J=14.1, 7.4 Hz, 1H), 1.73 (d, J=6.3 Hz, 1H), 1.44 (s, 9H), 1.35-1.28 (m, 2H), 0.92 (t, J=7.5 Hz, 3H). ¹³C NMR (151 MHz, CDCl₃) δ 155.57, 149.60, 148.69, 138.88, 134.42, 123.43, 78.88, 42.56, 41.21, 33.85, 27.92, 23.24, 10.41. HRMS (ESI-TOF) Calcd for $C_{15}H_{24}ClN_2O_2$ [M+H]⁺: 299.1521; found: 299.1520.

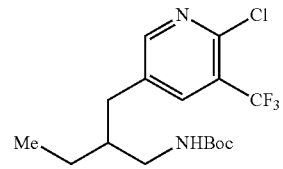 [SMILES: CCC(CNC(=O)OC(C)(C)C)Cc1cnc(Cl)c(C(F)(F)F)c1]

tert-butyl (2-((6-chloro-5-(trifluorotriethyl)pyridin-3-yl)methyl)butyl)carbamate (2b₆)

The general procedure was followed, except that the reaction was heated to 130° C. and stirred for 48 h. Compound 2b₆ was obtained as a white solid (42.5 mg, 58% yield) after purification by preparative TLC (eluent: hexane/EtOAc=2/1). ¹H NMR (400 MHz, CDCl₃) δ 8.38 (d, J=2.3 Hz, 1H), 7.82 (t, J=5.4 Hz, 1H), 4.54 (s, 1H), 3.22-2.95 (m, 2H), 2.69 (dd, J=14.2, 6.8 Hz, 1H), 2.59 (dd, J=14.2, 7.4 Hz, 1H), 1.77 (t, J=6.5 Hz, 1H), 1.44 (s, 9H), 1.37-1.29 (m, 2H), 0.94 (t, J=7.5 Hz, 3H). ¹³C NMR (151 MHz, CDCl₃) δ 155.56, 152.14, 146.04, 136.56, 134.86, 124.3 (q, J=33 Hz), 121.73 (q, J=273.2 Hz), 79.07, 42.43, 41.23, 33.77, 27.89, 23.32, 10.39. ¹⁹F NMR (400 MHz, CDCl₃) δ −63.86 (s), HRMS (ESI-TOF) Calcd for $C_{16}H_{23}ClF_3N_2O_2$ [M+H]⁺: 367.1395; found: 367.1392.

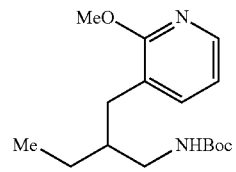

tert-butyl (2-((2-methoxypyridin-3-yl)methyl)butyl) carbamate (2b₇)

Following the general procedure, compound 2b₇ was obtained as a white solid (23.5 mg, 40% yield) after purification by preparative TLC (eluent: hexane/EtOAc=2/1). ¹H NMR (400 MHz, CDCl₃) 8.03 (dd, J=5.1, 1.8 Hz, 1H), 7.38 (d, J=7.2 Hz, 1H), 6.82 (dd, J=7.1, 5.0 Hz, 1H), 4.76 (s, 1H), 3.96 (s, 3H), 3.04 (ddt, J=46.5, 13.2, 5.3 Hz, 2H), 2.53 (dd, J=7.0, 3.0 Hz, 2H), 1.74 (p, J=6.3 Hz, 1H), 1.44 (s, 9H), 1.33 (p, J=7.3 Hz, 2H), 0.94 (t, J=7.4 Hz, 3H). ¹³C NMR (151 MHz, CDCl₃) δ 162.10, 156.16, 144.47, 138.86, 123.19, 116.79, 78.92, 53.27, 42.89, 40.34, 31.97, 28.44, 24.51, 11.16. HRMS (ESI-TOF) Calcd for $C_{16}H_{26}N_2O_3Na$ [M+Na]⁺: 317.1836; found: 317.1831.

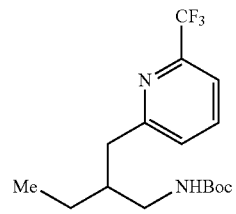 [SMILES: CCC(CNC(=O)OC(C)(C)C)Cc1cccc(C(F)(F)F)n1]

tert-butyl (2-((6-(trifluoromethyl)pyridin-2-yl) methyl)butyl)carbamate (2b₈)

Following the general procedure, compound 2b₈ was obtained as a white solid (50.5 mg, 76% yield) after purification by preparative TLC (eluent: hexane/EtOAc=2/1). $^1$H NMR (400 MHz, CDCl$_3$) δ 7.77 (t, J=7.8 Hz, 1H), 7.52-7.49 (m, 1H), 7.35 (d, J=7.9 Hz, 1H), 5.05 (s, 1H), 3.22-3.09 (m, 1H), 3.02 (dt, J=13.6, 6.6 Hz, 1H), 2.94-2.78 (m, 2H), 2.03 (dh, J=14.0, 7.4, 6.7 Hz, 1H), 1.43 (s, 9H), 1.38-1.29 (m, 2H), 0.95 (t, J=7.4 Hz, 3H). $^{13}$C NMR (151 MHz, CDCl$_3$) δ 161.30, 155.74, 147.13 (d, J=34.2 Hz), 137.04, 126.00, 121.06 (q, J=274.1 Hz), 117.24 (d, J=0.5 Hz), 78.42, 42.67, 39.94, 39.54, 27.92, 24.18, 10.73. $^{19}$F NMR (400 MHz, CDCl$_3$) δ −68.41 (s). HRMS (ESI-TOF) Calcd for C$_{16}$H$_{23}$F$_3$N$_2$O$_2$Na [M+Na]$^+$: 355.1604; found; 355.1603.

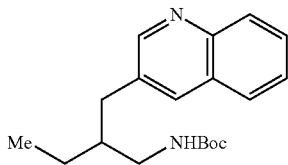 [SMILES: CCC(CNC(=O)OC(C)(C)C)Cc1cnc2ccccc2c1]

tert-butyl (2-(quinolin-3-ylmethyl)butyl)carbamate (2b$_9$)

The general procedure was followed, except that the reaction was heated to 130° C. and stirred for 48 h. Compound 2b$_9$ was obtained as a white solid (27.0 mg, 43% yield) after purification by preparative TLC (eluent: hexane/EtOAc=2/1). $^1$H NMR (400 MHz, CDCl$_3$) δ 8.75 (d, J=2.3 Hz, 1H), 8.12-8.05 (m, 1H), 7.96-7.88 (m, 1H), 7.77 (dd, J=8.2, 1.4 Hz, 1H), 7.66 (ddd, J=8.4, 6.9, 1.5 Hz, 1H), 7.53 (ddd, J=8.1 6.8, 1.2 Hz, 1H), 4.59 (s, 1H), 3.24-3.02 (m, 2H), 2.85-2.68 (m, 2H), 1.92-1.79 (m, 1H), 1.43 (s, 9H), 1.37 (dtd, J=14.5, 7.5, 5.7 Hz, 2H), 0.95 (t, J=7.4 Hz, 3H). $^{13}$C NMR (151 MHz, CDCl$_3$) δ 156.08, 152.17, 146.85, 135.14, 133.26, 129.12, 128.73, 128.05, 127.36, 126.64, 79.26, 43.21, 41.83, 35.42, 28.39, 23.79, 10.93, HRMS (ESI-TOF) Calcd for C$_{19}$H$_{26}$N$_2$O$_2$Na [M+Na]$^+$: 337.1886; found; 337.1885.

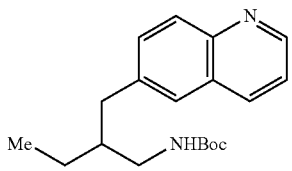 [SMILES: CCC(CNC(=O)OC(C)(C)C)Cc1ccc2ncccc2c1]

tert-butyl (2-(quinolin-6-ylmethyl)butyl)carbamate (2b$_{10}$)

The general procedure was followed, except that the reaction was heated to 130° C. and stirred for 48 h. Compound 2b$_{10}$ was obtained as a white solid (26.4 mg, 42% yield) after purification by preparative TLC (eluent: hexane/EtOAc=2/1). $^1$H NMR (600 MHz, CDCl$_3$) δ 8.86 (dd, J=4.3, 1.7 Hz, 1H), 8.09 (dt, J=8.1, 1.2 Hz, 1H), 8.04 (d, J=8.6 Hz, 1H), 7.58 (d, J=2.0 Hz, 1H), 7.55 (dd, J=8.7, 1.9 Hz, 1H), 7.38 (dd, J=8.2, 4.2 Hz, 1H), 4.55 (d, J=7.0 Hz, 1H), 3.14 (ddt, J=39.9, 12.8, 5.9 Hz, 2H), 2.76 (t, J=6.6 Hz, 2H), 1.88 (d, J=6.5 Hz, 1H), 1.42 (s, 9H), 1.40-1.34 (m, 2H), 0.95 (t, J=7.4 Hz, 3H). $^{13}$C NMR (151 MHz, CDCl$_3$) δ 155.61, 149.23, 146.59, 138.72, 135.20, 130.82, 128.80, 127.79, 126.62, 120.68, 78.68, 42.88, 41.40, 37.74, 27.94, 23.54, 10.51. HRMS (ESI-TOF) Calcd for C$_{19}$H$_{26}$N$_2$O$_2$Na (M+Na)$^+$: 337.1886; found; 337.1886.

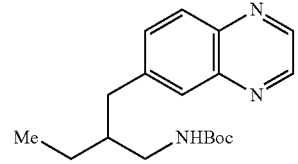 [SMILES: CCC(CNC(=O)OC(C)(C)C)Cc1ccc2nccnc2c1]

tert-butyl (2-(quinoxalin-6-ylmethyl)butyl)carbamate (2b$_{11}$)

The general procedure was followed, except that the reaction was heated to 130° C. and stirred for 48 h. Compound 2b$_{11}$ was obtained as a white solid (27.7 mg, 44% yield) after purification by preparative TLC (eluent: hexane/EtOAc=2/1). $^1$H NMR (400 MHz, CDCl$_3$) δ 8.81 (dd J=11.8, 1.8 Hz, 2H), 8.04 (d, J=8.6 Hz, 1H), 7.92-7.85 (m, 1H), 7.67-7.57 (m, 1H), 4.56 (s, 1H), 3.15 (dp, J=26.5, 6.9, 6.4 Hz, 2H), 2.83 (qd, J=13.9, 7.1 Hz, 2H), 1.92 (p, J=6.5 Hz, 1H), 1.43 (s, 9H), 1.40-1.35 (m, 2H), 0.95 (t, J=7.4 Hz, 3H). $^{13}$C NMR (151 MHz, CDCl$_3$) δ 155.59, 144.51, 143.85, 143.00, 142.56, 141.33, 131.50, 128.80, 128.18, 78.76, 42.84, 41.37, 37.83, 27.93, 23.46, 10.48, HRMS (ESI-TOF) Calcd for C$_{18}$H$_{25}$N$_3$O$_2$Na [M+Na]$^+$: 338.1839; found: 338.1839.

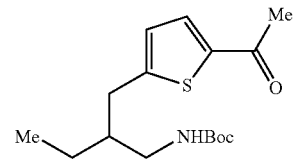 [SMILES: CCC(CNC(=O)OC(C)(C)C)Cc1ccc(C(C)=O)s1]

tert-butyl (2-((5-acetylthiophen-2-yl)methyl)butyl) carbamate (2b$_{12}$)

Following the general procedure, compound 2b$_{12}$ was obtained as a white solid (37.3 mg, 60% yield) after purification by preparative TLC (eluent: hexane/EtOAc=2/1). $^1$H NMR (400 MHz, CDCl$_3$) δ 7.53 (d, J=3.7 Hz, 1H), 6.84 (d, J=3.7 Hz, 1H), 4.55 (s, 1H), 3.11 (dtd, J=26.9, 13.5, 5.9 Hz, 2H), 2.82 (qd, J=14.9, 6.8 Hz, 2H), 2.51 (s, 3H), 1.83-1.75 (m, 1H), 1.44 (s, 9H), 1.40-1.33 (m, 2H), 0.94 (t, J=7.5 Hz, 3). $^{13}$C NMR (151 MHz, CDCl$_3$) δ 190.43, 156.07, 153.22, 142.56, 132.90, 126.86, 79.30, 43.06, 42.33, 32.64, 28.40, 26.48, 23.89, 10.96, HRMS (ESI-TOF) Calcd for C$_{16}$H$_{25}$NO$_3$SNa [M+Na]$^+$: 334.1447; found: 334.1445.

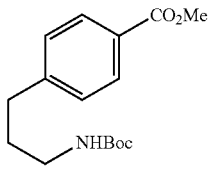 [SMILES: COC(=O)c1ccc(CCCNC(=O)OC(C)(C)C)cc1]

methyl 4-(3-((tert-butoxycarbonyl)amino)propyl) benzoate (2c)

Following the general procedure, compound 2c was obtained as a white solid (39.8 mg, 68% yield) after purification by preparative TLC (eluent: hexane/EtOAc=5/1). $^1$H NMR (600 MHz, CDCl$_3$) 7.98-7.92 (m, 2H), 7.26-7.22 (m, 2H), 3.90 (s, 3H), 3.15 (t, J=7.0 Hz, 2H), 2.72-2.67 (m, 2H), 1.83 (p, J=7.4 Hz, 2H), 1.44 (s, 9H). $^{13}$C NMR (150 MHz, CDCl$_3$) δ 167.08, 155.95, 147.12, 129.78, 128.38, 127.96, 79.23, 51.99, 40.15, 33.17, 31.46, 28.41. HRMS (ESI-TOF) Calcd for C$_{16}$H$_{23}$NO$_4$Na [M+Na]$^+$: 316.1519; found: 316.1518.

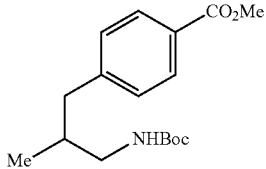

methyl 4-(3-((tert-butoxycarbonyl)amino)-2-methylpropyl)benzoate (2d, Monoarylation)

The general procedure was followed, except that the reaction was heated to 90° C. Mono- and di-arylation compounds were obtained as white solids (20.9 mg, 34% mono, 38% di, 72% total yield) after purification with preparative TLC (eluent: hexane/EtOAc=5/1). $^1$H NMR (600 MHz, CDCl$_3$) δ 7.98-7.93 (m, 2H), 7.24-7.20 (m, 2H), 4.58 (s, 1H), 3.90 (s, 3H), 3.06 (ddt, J=66.9, 13.9, 6.5 Hz, 2H), 2.76 (s, 1H), 2.41 (dd, J=13.5, 8.7 Hz, 1H), 2.01-1.88 (m, 1H), 1.44 (s, 9H), 0.86 (d, J=6.7 Hz, 3H). $^{13}$C NMR (151 MHz, CDCl$_3$) δ 167.10, 156.04, 146.06, 129.65, 129.09, 127.99, 79.22, 52.00, 46.39, 40.86, 35.71, 28.41, 17.24. HRMS (ESI-TOF) Calcd for C$_{17}$H$_{25}$NO$_4$Na [M+Na]$^+$: 330.1676; found: 330.1676.

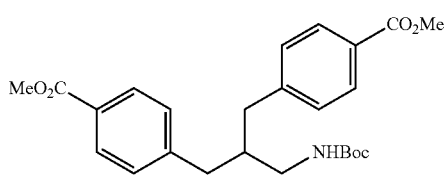 [SMILES: COC(=O)c1ccc(CC(CNC(=O)OC(C)(C)C)Cc2ccc(C(=O)OC)cc2)cc1]

dimethyl 4,4'-(2-(((tert-butoxycarbonyl)amino)methyl)propane-1,3-diyl)dibenzoate (2d, Diarylation)

The general procedure was followed, except that the reaction was heated to 90° C. Mono- and di-arylation compounds were obtained as white solids (34% mono, 33.5 mg, 36% di, 72% total yield) after purification with Preparative TLC (eluent: hexane/EtOAc=5/1). $^1$H NMR (600 MHz, CDCl$_3$) 7.97-7.93 (m, 4H), 7.20 (d, J=8.0 Hz, 4H), 4.52-4.44 (m, 1H), 3.90 (s, 6H), 3.08 (t, J=6.3 Hz, 2H), 2.64 (ddd, J=45.2, 13.9, 7.1 Hz, 4H), 2.21 (p, J=7.0 Hz, 1H), 1.42 (s, 9H). $^{13}$C NMR (151 MHz, CDCl$_3$) δ 166.99, 155.98, 145.58, 129.80, 129.05, 128.21, 79.35, 52.03, 43.59, 42.49, 38.36, 28.37. HRMS (ESI-TOF) Calcd for C$_{25}$H$_{31}$NO$_6$Na [M+Na]$^+$: 464.2044; found: 464.2045.

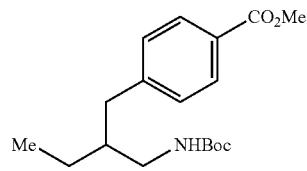 [SMILES: CCC(CNC(=O)OC(C)(C)C)Cc1ccc(C(=O)OC)cc1]

methyl 4-(2-(((tert-butoxycarbonyl)amino)methyl)butyl)benzoate (2e)

Following the general procedure, compound 2e was obtained as a white solid (44.3 mg, 69% yield) after purification by preparative TLC (eluent: hexane/EtOAc=5/1). $^1$H NMR (600 MHz, CDCl$_3$) δ 7.98-7.93 (m, 2H), 7.23 (d, J=8.0 Hz, 2H), 4.50 (s, 1H), 3.90 (s, 3H), 3.09 (ddt, J=41.9, 13.5, 5.9 Hz, 2H), 2.63 (qd, J=13.7, 7.1 Hz, 2H), 1.78 (p, J=6.5 Hz, 1H), 1.35-1.28 (m, 2H), 0.91 (t, J=7.5 Hz, 3H). $^{13}$C NMR (151 MHz, CDCl$_3$) δ 167.09, 156.04, 146.32, 129.68, 129.08, 127.95, 79.15, 51.99, 43.29, 41.87, 38.24, 28.40, 23.93, 10.93. HRMS (ESI-TOF) Calcd for C$_{15}$H$_{27}$NO$_4$Na [M+Na]$^+$: 344.1832; found: 344.1832.

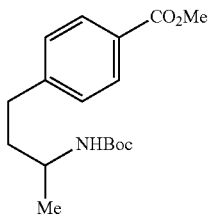 [SMILES: COC(=O)c1ccc(CCC(C)NC(=O)OC(C)(C)C)cc1]

methyl 4-(3-((tert-butoxycarbonyl)amino)butyl)benzoate (2f)

The general procedure was followed, except that 50 mol % TDG4 was used. Compound 2f was obtained as a white solid (54.6 mg, 89% yield) after purification with preparative TLC (eluent: hexane/EtOAc=5/1). $^1$H NMR (600 MHz, CDCl$_3$) δ 7.98-7.92 (m, 2H), 7.25 (d, J=8.2 Hz, 2H), 4.38 (s, 1H), 3.90 (s, 3H), 3.73 (d, J=17.3 Hz, 1H), 2.71 (td, J=7.7, 4.8 Hz, 2H), 1.74 (dd, J=8.7, 5.8 Hz, 2H), 1.45 (s, 9H), 1.16 (d, J=6.6 Hz, 3H). $^{13}$C NMR (151 MHz, CDCl$_3$) δ 167.11, 155.34, 147.51, 129.76, 128.38, 127.86, 79.12, 51.97, 46.34, 38.79, 32.59, 28.43, 28.04, 21.38. HRMS (ESI-TOF) Calcd for C$_{17}$H$_{25}$NO$_4$Na [M+Na]$^+$: 330.1676; found: 330.1676.

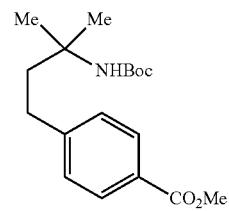

methyl 4-(3-((tert-butoxycarbonyl)amino)-3-methylbutyl)benzoate (2g, Monoarylation)

Following the general procedure, mono- and di-arylation compounds were obtained as white solids (10.3 mg, 16% mono, 45% di, 61% total yield) after purification with preparative TLC (eluent: hexane/EtOAc=5/1). $^1$H NMR (600 MHz, CDCl$_3$) δ 7.96-7.92 (m, 2H), 7.26-7.24 (m, 2H), 4.45 (s, 1H), 3.90 (s, 3H), 2.67-2.59 (m, 2H), 1.99 (t, J=8.6 Hz, 2H), 1.45 (s, 9H), 1.31 (s, 6H). $^{13}$C NMR (151 MHz, CDCl$_3$) δ 166.69, 147.69, 129.27, 127.97, 127.26, 126.79, 78.37, 51.95, 51.50, 41.10, 30.49, 28.00, 27.01. HRMS (ESI-TOF) Calcd for C$_{18}$H$_{27}$NO$_4$Na [M+Na]$^+$: 344.1832; found: 344.1825.

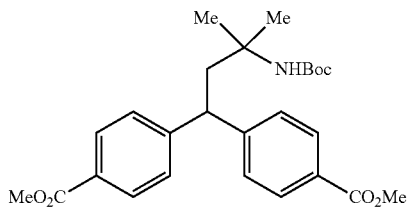 [SMILES: COC(=O)c1ccc(C(CC(C)(C)NC(=O)OC(C)(C)C)c2ccc(C(=O)OC)cc2)cc1]

dimethyl 4,4'-(3-((tert-butoxycarbonyl)amino)-3-methylbutane-1,1-diyl)dibenzoate (2g, Diarylation)

Following the general procedure, mono- and di-arylation compounds were obtained as white solids (16% mono, 40.9 mg, 45% di, 61% total yield) after purification with preparative TLC (eluent: hexane/EtOAc=5/1). $^1$H NMR (600 MHz, CDCl$_3$) δ 7.98-7.89 (m, 4H), 7.40-7.31 (m, 4H), 4.26 (s, 1H), 4.18 (t, J=6.7 Hz, 1H), 3.88 (s, 6H), 2.59 (d, J=6.7 Hz, 2H), 1.37 (s, 9H), 1.17 (s, 6H). $^{13}$C NMR (151 MHz, CDCl$_3$) δ 166.86, 154.09, 150.23, 130.03, 128.27, 127.86, 127.25, 78.82, 52.80, 52.01, 47.93, 44.23, 28.38. HRMS (ESI-TOF) Calcd for C$_{26}$H$_{33}$NO$_6$Na [M+Na]$^+$: 478.2200: found: 473.2201.

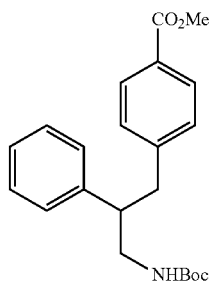 [SMILES: COC(=O)c1ccc(CC(CNC(=O)OC(C)(C)C)c2ccccc2)cc1]

methyl 4-(3-((tert-butoxycarbonyl)amino)-2-phenyl-propyl)benzoate (2h)

Following the general procedure, compound 2h was obtained as a white solid (44.3 mg, 60% yield) after purification by preparative TLC (eluent: hexane/EtOAc=5/1). $^1$H NMR (600 MHz, CDCl$_3$) 7.85 (d, J=7.9 Hz, 2H), 7.28-7.24 (m, 2H), 7.22-7.18 (m, 1H), 7.10-7.05 (m, 4H), 4.41 (s, 1H), 3.87 (s, 3H), 3.58 (p, J=6.2 Hz, 1H), 3.26 (ddd, J=12.9, 8.4, 4.4 Hz, 1H), 3.08 (d, J=6.5 Hz, 1H), 3.03 (dd, J=13.6, 6.0 Hz, 1H), 2.90 (dd, J=13.5, 8.7 Hz, 1H), 1.39 (s, 9H). $^{13}$C NMR (151 MHz, CDCl$_3$) $^{13}$C NMR (151 MHz, CDCl$_3$) δ 167.06, 155.84, 145.12, 141.38, 129.52, 129.06, 128.64, 127.98, 127.88, 126.93, 79.30, 51.95, 47.68, 45.51, 40.51, 28.34. HRMS (ESI-TOF) Calcd for C$_{22}$H$_{27}$NO$_4$Na [M+Na]$^+$: 392.1832; found: 392.1832.

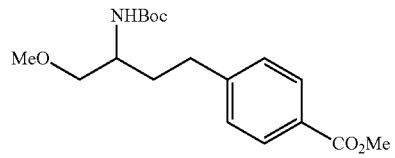 [SMILES: COCC(CCc1ccc(C(=O)OC)cc1)NC(=O)OC(C)(C)C]

methyl 4-(3-((tert-butoxycarbonyl)amino)-4-methoxybutyl)benzoate (2i)

Following the general procedure, compound 2i was obtained as a white solid (34.4 mg, 51% yield) after purification by preparative TLC (eluent: hexane/EtOAc=5/1). $^1$H NMR (600 MHz, CDCl$_3$) 7.95 (d, J=8.0 Hz, 2H), 7.28-7.24 (m, 2H), 4.77 (d, J=7.8 Hz, 1H), 3.90 (d, J=0.9 Hz, 3H), 3.76 (s, 1H), 3.39 (d, J=4.2 Hz, 2H), 3.33 (d, J=0.9 Hz, 3H), 2.72 (dtd, J=15.9, 14.0, 7.4 Hz, 2H) 1.93-1.75 (m, 2H), 1.45 (d, J=0.9 Hz, 9H). $^{13}$C NMR (151 MHz, CDCl$_3$) δ 167.15, 155.63, 147.49, 129.75, 128.43, 127.87, 79.32, 74.54, 59.13, 51.99, 50.11, 33.75, 32.58, 28.43. HRMS (ESI-TOF) Calcd for C$_{18}$H$_{27}$NO$_5$Na [M+Na]$^+$: 360.1781; found: 360.1781.

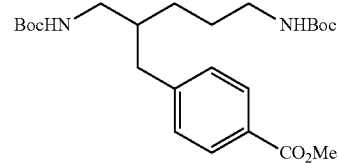 [SMILES: COC(=O)c1ccc(CC(CCCNC(=O)OC(C)(C)C)CNC(=O)OC(C)(C)C)cc1]

methyl 4-(5-((tert-butoxycarbonyl)amino)-2-(((tert-butoxycarbonyl)amino)methyl)pentyl)-benzoate (2j)

The general procedure was followed, except 8.0 eq of Boc$_2$O was used during the Boc protection step. Compound 2j was obtained as a white solid (41.4 mg, 46% yield) after purification by preparative TLC (eluent: hexane/EtOAc=5/1). $^1$H NMR (600 MHz, CDCl$_3$) δ 7.95 (d, J=8.3 Hz, 2H), 7.22 (d, J=8.1 Hz, 2H), 4.58 (d, J=29.1 Hz, 2H), 3.90 (s, 3H), 3.07 (t, J=7.6 Hz, 4H), 2.62 (qd, J=13.8, 7.2 Hz, 2H), 1.86 (p, J=6.3 Hz, 1H), 1.54 (s, 1H), 1.43 (d, J=3.3 Hz, 19H), 1.35-1.23 (m, 2H). $^{13}$C NMR (151 MHz, CDCl$_3$) δ 167.02, 156.19, 156.05, 145.91, 129.77, 129.04, 128.10, 79.31, 79.07, 52.01, 43.24, 40.54, 40.25, 38.69, 28.43, 28.29, 26.93. HRMS (ESI-TOF) Calcd for C$_{24}$H$_{38}$N$_2$O$_6$Na [M+Na]$^+$: 473.2622; found: 473.2621.

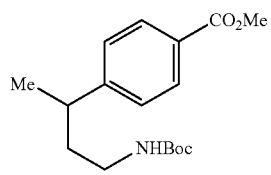 [SMILES: COC(=O)c1ccc(C(C)CCNC(=O)OC(C)(C)C)cc1]

methyl 4-(4-((tert-butoxycarbonyl)amino)butan-2-yl)benzoate (2k)

The general procedure was followed, except that the reaction was performed at 150° C. in HFIP/HOAc=2/1 solution (1.0 mL) with 30 eq. H$_2$O additive (6.0 mmol). Compound 2k was obtained as a white solid (40.5 mg, 66% yield) after purification with preparative TLC (eluent: hexane/EtOAc=5/1). $^1$H NMR (600 MHz, CDCl$_3$) δ 7.98-7.95 (m, 2H), 7.26-7.24 (m, 2H), 4.44 (s, 1H), 3.90 (s, 3H), 3.01 (dtd, J=20.1, 13.5, 12.6, 6.4 Hz, 2H), 2.82 (h, J=7.1 Hz, 1H), 1.84-1.73 (m, 2H), 1.42 (s, 9H), 1.28 (d, J=6.9 Hz, 3H). $^{13}$C NMR (151 MHz, CDCl$_3$) δ 167.05, 155.83, 152.14, 129.92, 128.19, 126.93, 79.18, 52.00, 39.00, 38.10, 37.76, 28.40, 22.00. HRMS (ESI-TOF) Calcd for C$_{17}$H$_{25}$NO$_4$Na [M+Na]$^+$: 330.1676; found: 330.1676.

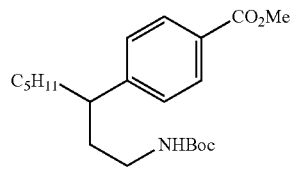

methyl 4-(1-((tert-butoxycarbonyl)amino)octan-3-yl)benzoate (2l)

The general procedure was followed, except that the reaction was performed at 150° C. in HFIP/HOAc=2/1 solution (1.0 mL) with 30 eq. H$_2$O additive (6.0 mmol). Compound 2l was obtained as a white solid (31.2 mg, 43% yield) after purification with preparative TLC (eluent: hexane/EtOAc=5/1). $^1$H NMR (600 MHz, CDCl$_3$) δ 7.96 (d, J=8.3 Hz, 2H), 7.21 (d, J=8.3 Hz, 2H), 4.42 (s, 1H), 3.90 (s, 3H), 2.93 (dtd, J=19.4, 11.5, 10.2, 4.5 Hz, 2H), 2.62 (tt, J=9.8, 5.2 Hz, 1H), 1.72 (ddt, J=13.7, 9.6, 6.9 Hz, 1H), 1.64 (ddt, J=15.0, 10.0, 5.0 Hz, 1H), 1.57 (qd, J=9.5, 4.7 Hz, 1H), 1.42 (s, 9H), 1.27-1.11 (m, 6H), 1.06 (dtd, J=14.8, 7.3, 4.5 Hz, 1H), 0.84-0.80 (m, 3H). $^{13}$C NMR (151 MHz, CDCl$_3$) δ 161.09, 155.81, 150.75, 129.85, 128.21, 127.59, 79.12, 51.99, 43.82, 39.01, 36.79, 36.57, 31.75, 28.39, 27.05, 22.48. 14.00. HRMS (ESI-TOF) Calcd for C$_{21}$H$_{33}$NO$_4$Na [M+Na]$^+$: 386.2302; found: 386.2302.

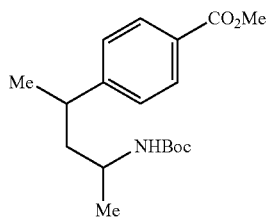

methyl 4-(4-((tert-butoxycarbonyl)amino)pentan-2-yl)benzoate (2m)

The general procedure was followed, except that 50 mol % TDG4 was used. Compound 2m was obtained as a white solid (54.6 mg, 85% yield, 2.6/1 d.r.) after purification with preparative TLC (eluent: hexane/EtOAc=5/1). $^1$H NMR (600 MHz, CDCl$_3$) δ 7.99-7.94 (m, 2H), 7.26 (dd, J=8.2, 4.7 Hz, 2H), 4.26 (dd, J=18.0, 8.6 Hz, 1H), 3.90 (s, 3H), 3.52 (s, 1H), 2.88 (dt, J=14.0, 7.4 Hz, 1H), 1.66 (td, J=8.4, 4.4 Hz, 2H), 1.43 (s, 9H), 1.27 (dd, J=6.9, 3.8 Hz, 3H), 1.08 (d, J=6.5 Hz, 3H). $^{13}$C NMR (151 MHz, CDCl$_3$) δ 166.63, 154.56, 151.99, 129.38, 127.63, 126.60, 126.43, 78.51, 51.49, 45.24, 44.40, 36.50, 27.95. HRMS (ESI-TOF) Calcd for C$_{18}$H$_{27}$NO$_4$Na [M+Na]$^+$: 344.1832; found: 344.1832.

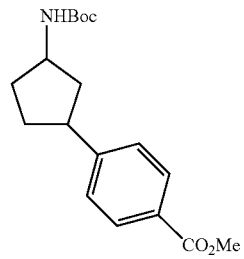 [SMILES: COC(=O)c1ccc(C2CCC(NC(=O)OC(C)(C)C)C2)cc1]

methyl 4-(3-((tert-butoxycarbonyl)amino)cyclopentyl)benzoate (2n)

The general procedure was followed, except that 50 mol % TDG4 was used. Compound 2n was obtained as a white solid (26.1 mg, 41% yield, single diastereomer (cis)) after purification with preparative TLC (eluent: hexane/EtOAc=5/1). $^1$H NMR (600 MHz, CDCl$_3$) δ 7.96 (d, J=8.3 Hz, 2H), 7.28 (d, J=8.3 Hz, 2H), 4.62 (s, 1H), 4.10 (s, 1H), 3.90 (s, 3H), 3.12 (ddd, J=17.4, 10.3, 7.5 Hz, 1H), 2.53 (dt, J=13.2, 6.9 Hz, 1H), 2.21-2.07 (m, 2H), 1.76 (dtd, J=12.8, 9.9, 9.4, 6.9 Hz, 1H), 1.66-1.59 (m, 1H), 1.45 (s, 9H). $^{13}$C NMR (151 MHz, CDCl$_3$) δ 166.58, 155.01, 150.15, 129.29, 127.55, 126.48, 78.80, 51.54, 43.36, 41.26, 32.45, 31.38, 27.97. HRMS (ESI-TOF) Calcd for C$_{18}$H$_{25}$NO$_4$Na [M+Na]$^+$: 342.1676; found: 342.166. The stereochemistry was determined by 2D NOE analysis.

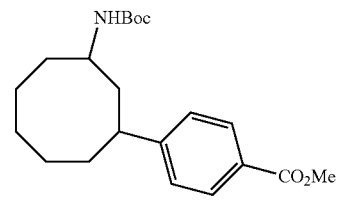 [SMILES: COC(=O)c1ccc(C2CCCCCC(NC(=O)OC(C)(C)C)C2)cc1]

methyl 4-(3-((tert-butoxycarbonyl)amino)cyclooctyl)benzoate (2o, Monoarylation)

Following the general procedure, mono- and di-arylation compounds were obtained as white solids (23.8 mg, 33% mono, 43% di, 76% total yield) after purification with preparative TLC (eluent: hexane/EtOAc=5/1). $^1$H NMR (600 MHz, CDCl$_3$) δ 7.94 (d, J=8.3 Hz, 2H), 7.24 (d, J=8.3 Hz, 2H), 4.50 (s, 1H), 3.90 (s, 3H), 3.83 (s, 1H), 2.91 (s, 1H), 2.00-1.91 (m, 3H), 1.90-1.74 (m, 3H), 1.65 (td, J=14.7, 11.8, 8.1 Hz, 6H), 1.41 (s, 9H). $^{13}$C NMR (151 MHz, CDCl$_3$) δ 167.11, 154.95, 154.81, 129.84, 127.72, 126.81, 79.10, 51.96, 50.71, 44.02, 41.42, 35.09, 33.35, 28.44, 26.95, 24.32. 22.43. HRMS (ESI-TOF) Calcd for C$_{21}$H$_{31}$NO$_4$Na [M+Na]$^+$: 384.2145; found: 384.2144. The stereochemistry was determined by 2D NOE analysis.

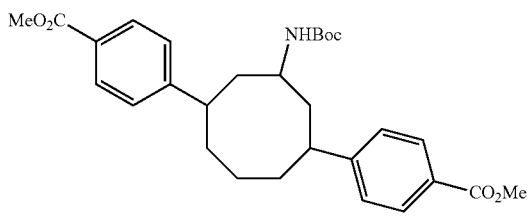 [SMILES: COC(=O)c1ccc(C2CCCC(c3ccc(C(=O)OC)cc3)CC(NC(=O)OC(C)(C)C)C2)cc1]

dimethyl 4,4'-(3-((tert-butoxycarbonyl)amino)cyclooctane-1,5-diyl)dibenzoate (2o, Diarylation)

Following the general procedure, mono- and di-arylation compounds were obtained as white solids (33% mono, 42.6 mg, 43% di, 76% total yield) after purification with preparative TLC (eluent: hexane/EtOAc=5/1). $^1$H NMR (600 MHz, CDCl$_3$) δ 7.99-7.94 (m, 4H), 7.30-7.24 (m, 4H), 4.64 (s, 1H), 3.90 (s, 6H), 3.79 (d, J=31.2 Hz, 1H), 3.12 (s, 2H), 2.15-1.86 (m, 8H), 1.77 (qd, J=10.6, 9.9, 4.5 Hz, 2H), 1.36 (s, 9H). $^{13}$C NMR (151 MHz, CDCl$_3$) δ 167.04, 154.62, 154.51, 129.94, 127.88, 126.85, 79.25, 52.00, 42.73, 42.16, 35.77, 28.37, 23.37. HRMS (ESI-TOF) Calcd for C$_{29}$H$_{37}$NO$_6$Na [M+Na]$^+$: 518.2513, found: 518.2513. The stereochemistry was determined by 2D NOE analysis.

2.3 Large Scale Reaction with the Production of Free Arylated Amine

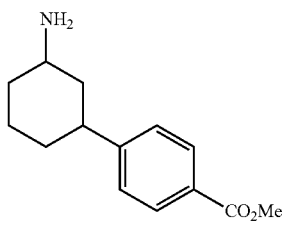 [SMILES: COC(=O)c1ccc(C2CCCC(N)C2)cc1]

methyl 4-(3-aminocyclohexyl)benzoate (2p)

The general procedure for setting up the reaction was followed. After the reaction, the mixture was cooled to room temperature, filtered through Celite and mixed with 1M aqueous HCl (2.0 mL). After being stirred at room temperature for 30 min, the mixture was transferred to a separate funnel and the organic phase was discarded. The water phase was washed with CH$_2$Cl$_2$ (5.0 mL), basified by 4M aqueous NaOH until pH>12 and extracted with CH$_2$Cl$_2$ (4×15.0 mL). The combined organic phase was dried over Na$_2$SO$_4$ and concentrated in Vacuo to obtain the pure product without any further purification as a pale yellow oil (284.3 mg, 61% yield). $^1$H NMR (600 MHz, CDCl$_3$) δ 7.99-7.93 (m, 2H), 7.28-7.23 (m, 2H), 3.89 (s, 3H), 2.81 (tt, J=11.1, 3.9 Hz, 1H), 2.64 (tt, J=12.2, 3.4 Hz, 1H), 2.02 (dtt, J=14.2, 3.8, 1.6 Hz, 1H), 1.97-1.91 (m, 1H), 1.89 (dp, J=13.2, 3.3 Hz, 1H), 1.84 (dddd, J=14.5, 5.1, 3.3, 1.7 Hz, 1H), 1.46 (qt, J=13.1, 3.4 Hz, 2H), 1.35 (td, J=12.6, 3.5 Hz, 1H), 1.27 (td, J=12.3, 11.0 Hz, 1H), 1.10 (tdd, J=12.8, 11.2, 3.7 Hz, 1H). $^{13}$C NMR (151 MHz, CDCl$_3$) δ 166.62, 151.69, 129.30, 127.49, 126.36, 51.49, 50.34, 43.70, 42.97, 35.76, 32.77, 24.76. HRMS (ESI-TOF) Calcd for C$_{14}$H$_{19}$NO$_2$Na [M+Na]$^+$: 256.1313; found: 256.1314.

2.4 Synthesis of 1,2,3,4-tetrahydronaphthyridine

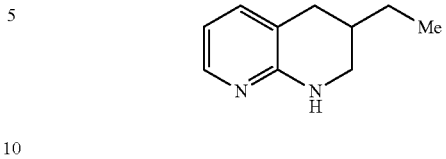

3-ethyl-1,2,3,4-tetrahydro-1,8-naphthyridine (2q)

Following the general procedure before Boc protection workup, 1,2,3,4-tetrahydronaphthyridine was obtained as a brown solid (22.7 mg, 70%) after purification with preparative TLC (eluent: hexane/EtOAc=1/1). $^1$H NMR (600 MHz, CDCl$_3$) δ 7.72-7.65 (m, 1H), 7.19 (dq, J=7.2, 1.3 Hz, 1H), 7.08 (s, 1H), 6.44 (dd, J=7.1, 5.5 Hz, 1H), 3.48 (dtd, J=11.9, 3.8, 2.0 Hz, 1H), 3.03 (dd, J=11.9, 9.4 Hz, 1H), 2.78 (ddd, J=15.9, 4.5, 2.0 Hz, 1H), 2.39 (ddt, J=15.9, 10.3, 1.2 Hz, 1H), 1.77 (tdt, J=14.0, 6.8, 4.2 Hz, 1H), 1.38 (dq, J=14.3, 7.3 Hz, 2H), 0.98 (t, J=7.5 Hz, 3H). $^{13}$C NMR (151 MHz, CDCl$_3$) δ 155.35, 144.01, 136.90, 117.61, 111.21, 45.71, 32.46, 31.99, 25.46, 10.99. HRMS (ESI-TOF) Calcd for C$_{10}$H$_{14}$N$_2$Na [M+Na]$^+$: 185.1049; found: 185.1049.

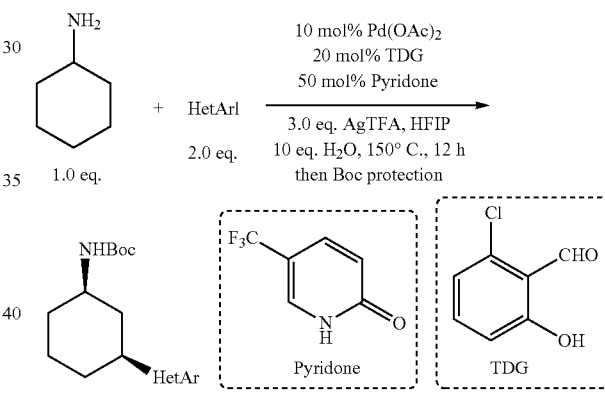

C—H Heteroarylation

To a long 20 ml reaction tube charged with a magnetic stirring bar was added Pd(OAc)$_2$ (2.3 mg, 0.01 mmol), 2-chloro-6-hydroxybenzaldehyde (3.1 mg, 0.02 mmol), pyridone (8.1 mg, 0.05 mmol), AgOTFA (66.3 mg, 0.3 mmol), Heteroaryl Iodide (0.2 mmol), cyclohexylamine (11.5 uL, 0.1 mmol) and H$_2$O (18 uL). The tube was well sealed and stirred at room temperature for 5 mins before moving to a 150° C. heating plate. After 12 h, the reaction was cooled to room temperature and EtOH (2.0 mL) was added. The mixture was filtered through a pad of Celite (3 cm) and washed with EtOH (1.0 mL×3). The filtrates were combined and evaporated under vacuum.

Boc Protection

The residue was dissolved in THF (1.0 mL) and HCl$_{(aq.)}$ (2N, 0.5 mL) was added. The brown mixture was stirred at room temperature for 1 h. NaOH$_{(aq.)}$ (10 M, 0.2 mL) was slowly added to the mixture under an ice-water bath. Then di-tert-butoxycarbonyl anhydride Boc$_2$O (0.1 mL) was added. The mixture was allowed to warm up to room temperature and stirred overnight. Ethyl acetate (1.0 mL) was added and the top layer (organic layer) was taken and passed through a plug of silica (3 cm). Ethyl acetate (2.0 mL×3) was used to extract the remaining aqueous layer and washed through the above silica. The filtrate was combined and evaporated to afford the crude Boc protected amine. The residue was applied to column chromatography to get the pure compound.

What is claimed is:

1. A method for preparing a compound of formula (II):

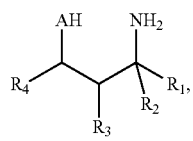

wherein:
AH is aryl or heteroaryl, each optionally substituted with one or more substituents independently selected from the group consisting of halo, nitro, alkyl, haloalkyl, formyl, alkoxycarbonyl, alkoxy, and aryl;
$R_1$ is hydrogen or alkyl;
$R_2$ is hydrogen or alkyl;
$R_3$ is hydrogen or alkyl; and
$R_4$ is hydrogen or alkyl; or
$R_2$ and $R_4$, together with the carbon atoms to which they are bonded, form a cycloalkyl;
the method comprising:
(1) contacting a compound of formula (I):

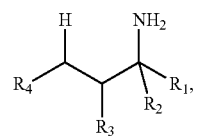

wherein:
Ri is hydrogen or alkyl;
$R_2$ is hydrogen or alkyl;
$R_3$ is hydrogen or alkyl; and
$R_4$ is hydrogen or alkyl; or
$R_2$ and $R_4$, together with the carbon atoms to which they are bonded, form a cycloalkyl;
with an aryl iodide or heteroaryl iodide of formula:

AH—I, wherein:
AH is aryl or heteroaryl, each optionally substituted with one or more substituents independently selected from the group consisting of halo, nitro, alkyl, haloalkyl, formyl, alkoxycarbonyl, alkoxy, and aryl;
in a reaction milieu comprising palladium (II) acetate and a catalytic transient directing group of formula (TDG):

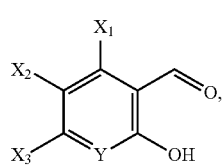

wherein:
Y is $CX_4$ or N;
$X_1$ is hydrogen, alkyl, haloalkyl, alkylamino, alkoxy, or aryl;
$X_2$ is hydrogen, alkyl, haloalkyl, alkylamino, alkoxy, or aryl;
$X_3$ is hydrogen, alkyl, haloalkyl, alkylamino, alkoxy, or aryl; and
$X_4$ is hydrogen, alkyl, haloalkyl, alkylamino, alkoxy, or aryl; or
$X_1$ and $X_2$, together with the carbon atoms to which they are bonded, form a fused 5-, 6-, or 7-membered cycloalkyl; or
$X_2$ and $X_3$, together with the carbon atoms to which they are bonded, form a fused 5-, 6-, or 7-membered cycloalkyl; or
$X_3$ and $X_4$, together with the carbon atoms to which they are bonded, form a fused 5-, 6-, or 7-membered cycloalkyl;
to provide a compound of formula (II) as defined above; and
(2) optionally contacting the compound of formula (II) above with a compound of formula:

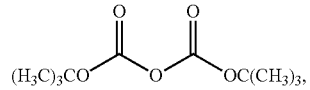

to provide a compound of formula (III):

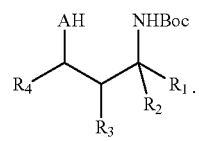

wherein:
AH is aryl or heteroaryl, each optionally substituted with one or more substituents independently selected from the group consisting of halo, nitro, alkyl, haloalkyl, formyl, alkoxycarbonyl, alkoxy, and aryl;
Ri is hydrogen or alkyl;
$R_2$ is hydrogen or alkyl;
$R_3$ is hydrogen or alkyl; and
$R_4$ is hydrogen or alkyl; or
$R_2$ and $R_4$, together with the carbon atoms to which they are bonded, form a cycloalkyl.

2. The method of claim 1, wherein AH is optionally substituted aryl.

3. The method of claim 2, wherein the reaction milieu further comprises silver trifluoroacetate.

4. The method of claim 1, wherein AH is optionally substituted heteroaryl.

5. The method of claim 4, wherein the reaction milieu further comprises silver trifluoroacetate, pyridone, or a combination of silver trifluoroacetate and pyridone.

6. The method of claim 1, wherein the catalytic transient directing group of formula (TDG) is of formula (TDG4):

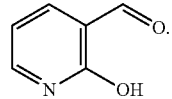
(TDG4)

7. The method of claim 1, wherein the method comprises contacting the compound of formula (II) with a compound of formula:

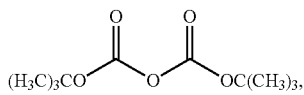

to provide a compound of formula (III):

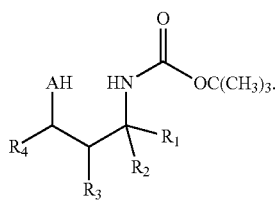
(III)

8. The method of claim 7, wherein AH is optionally substituted aryl.

9. The method of claim 8, wherein the compound of formula (III) is selected from the group consisting of:

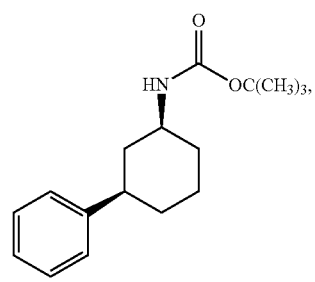
2a₁

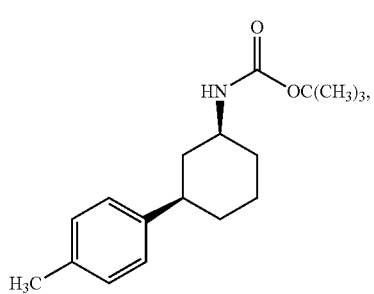
2a₂

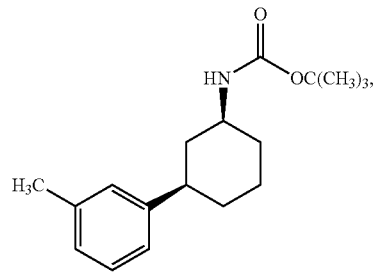
2a₃

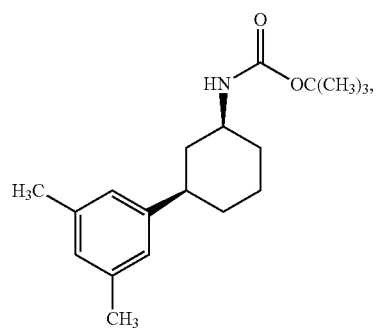
2a₄

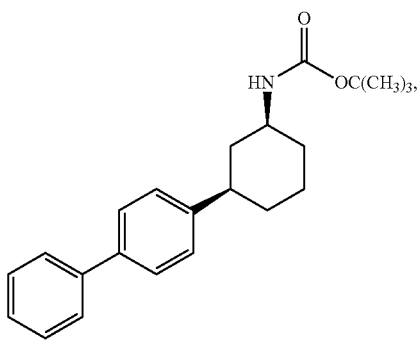
2a₅

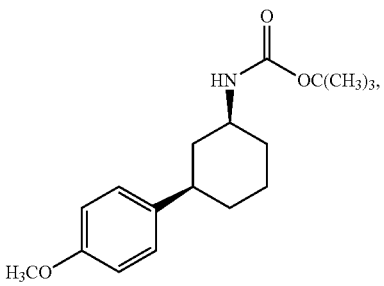
2a₆

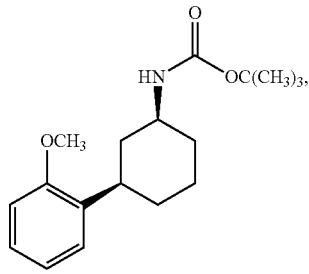
2a₇

2a8
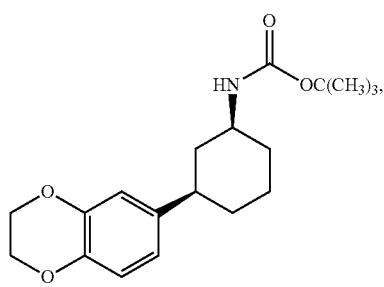
2a9
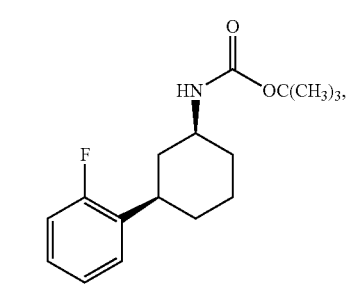
2a10
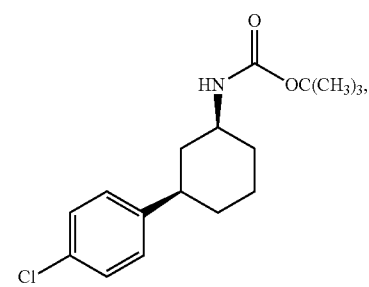
2a11
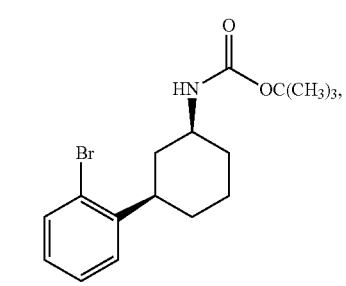
2a13
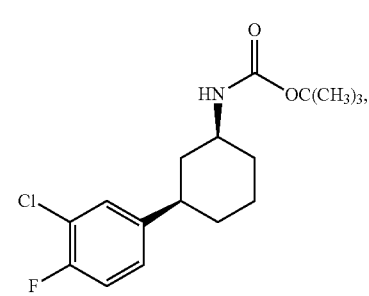
2a14
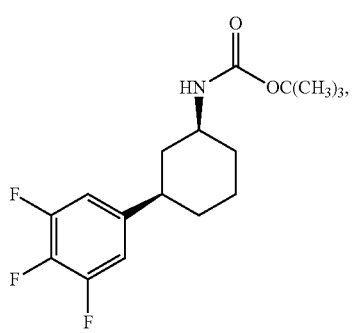
2a15
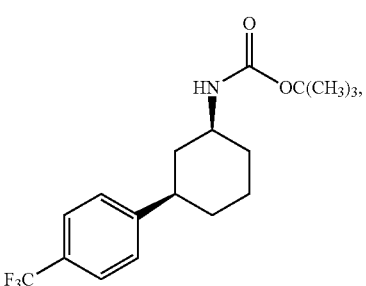
2a16
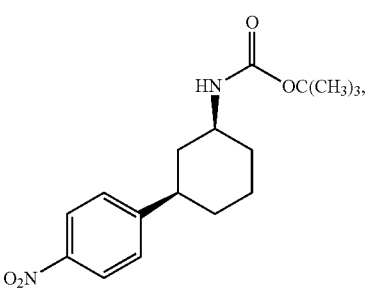
2a17
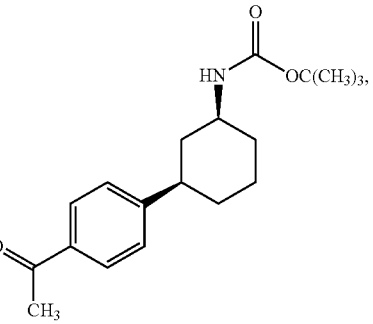
2a18
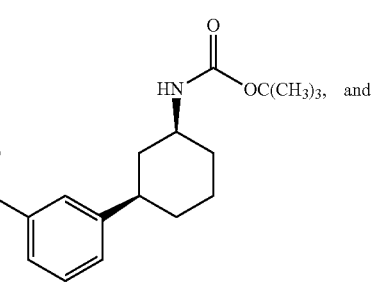

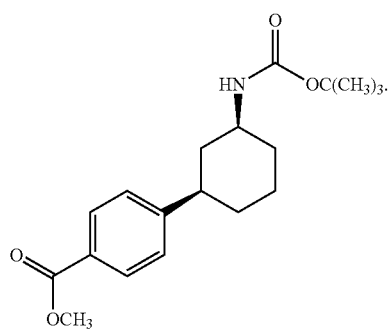
2a₁₉
10. The method of claim 7, wherein AH is optionally substituted heteroaryl.
11. The method of claim 10, wherein the compound of formula (III) is selected from the group consisting of:
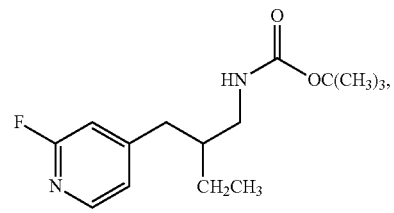
2b₁
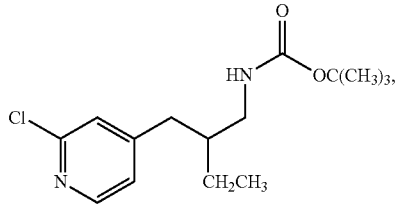
2b₂
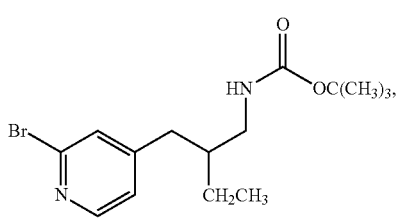
2b₃
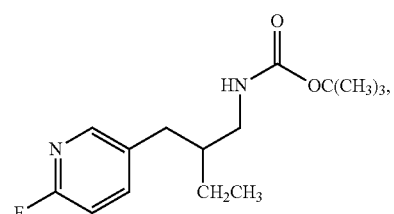
2b₄
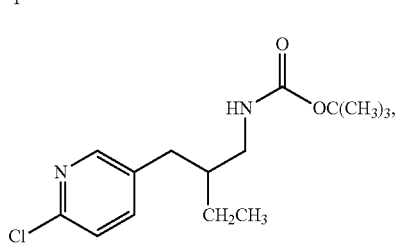
2b₅
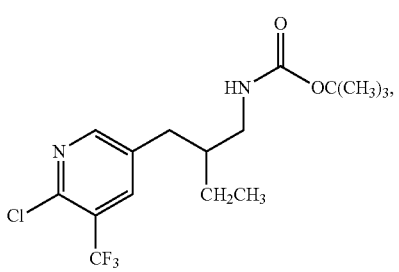
2b₆
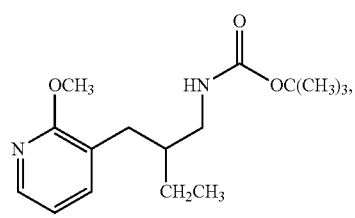
2b₇
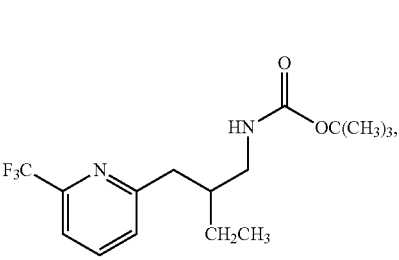
2b₈
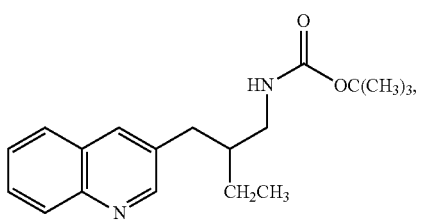
2b₉
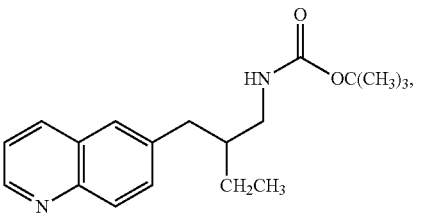
2b₁₀
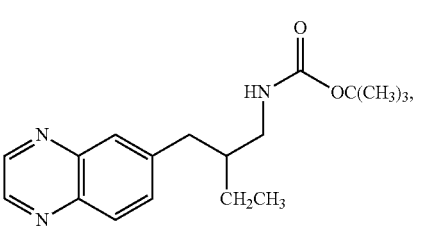
2b₁₁

-continued
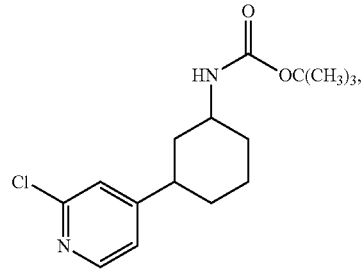
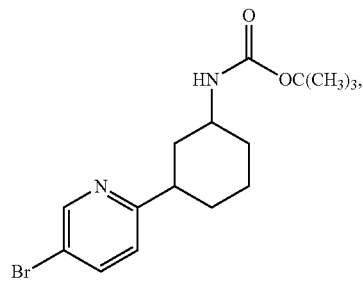
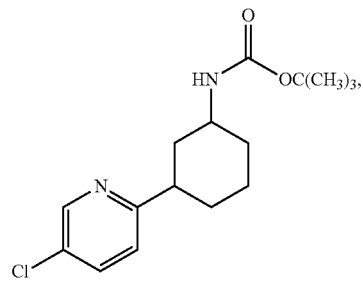
-continued
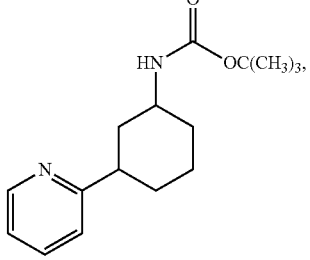
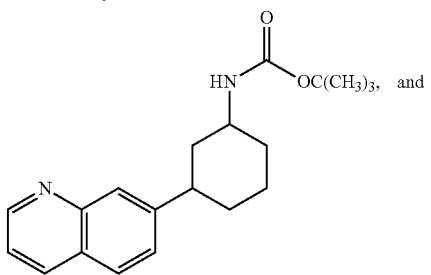 and
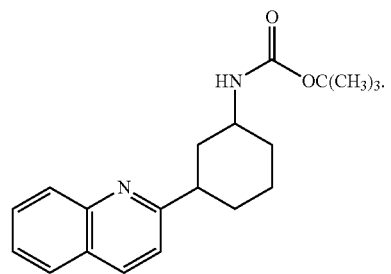
* * * * *